(12) United States Patent
Galbierz et al.

(10) Patent No.: US 11,064,989 B2
(45) Date of Patent: Jul. 20, 2021

(54) MULTI-PLY RETRACTOR/STABILIZER AND WOUND EXPOSURE DEVICE AND METHOD OF USE

(71) Applicant: GSQUARED MEDICAL LLC, Brentwood, TN (US)

(72) Inventors: Thomas R. Galbierz, Brentwood, TN (US); Michael A. Galbierz, St. Louis, MO (US)

(73) Assignee: GSQUARED MEDICAL LLC, Brentwood, TN (US)

(*) Notice: Subject to any disclaimer, the term of this patent is extended or adjusted under 35 U.S.C. 154(b) by 203 days.

(21) Appl. No.: 16/302,544

(22) PCT Filed: May 19, 2017

(86) PCT No.: PCT/US2017/033593
§ 371 (c)(1),
(2) Date: Nov. 16, 2018

(87) PCT Pub. No.: WO2017/205212
PCT Pub. Date: Nov. 30, 2017

(65) Prior Publication Data
US 2019/0159768 A1 May 30, 2019

Related U.S. Application Data

(60) Provisional application No. 62/341,730, filed on May 26, 2016.

(51) Int. Cl.
*A61B 17/02* (2006.01)
*A61F 5/37* (2006.01)
(Continued)

(52) U.S. Cl.
CPC ............ *A61B 17/02* (2013.01); *A61B 46/20* (2016.02); *A61F 5/37* (2013.01); *A61B 46/40* (2016.02);
(Continued)

(58) Field of Classification Search
CPC . A61B 17/02; A61B 2046/205; A61B 17/085; A61F 5/37; A61F 5/3784
See application file for complete search history.

(56) References Cited

U.S. PATENT DOCUMENTS 1,783,512 A 12/1930 Mather
3,522,800 A 8/1970 Lesser
(Continued)

FOREIGN PATENT DOCUMENTS

EP 0081987 B1 10/1985
EP 0051935 B1 11/1986
(Continued)

OTHER PUBLICATIONS

International Search Report for corresponding PCT/2017/033593, dated Aug. 22, 2017 mailed.
(Continued)

*Primary Examiner* — Andrew Yang
(74) *Attorney, Agent, or Firm* — Sandberg Phoenix & von Gontard, P.C.

(57) ABSTRACT

A multi-ply adhesive retraction device is provided which comprises a top layer, a backing layer and a stretchable middle layer between the top and backing layers. A middle-ply adhesive applied to substantially the entirety of the middle layer bottom surface to removably adhere the backing layer to the middle layer bottom surface. The device includes at least one bottom ply tab integral with the device which is operable to remove at least a portion of the backing layer from the middle layer to expose the adhesive of the
(Continued)

middle layer. Additionally, the device includes at least one top ply tab which is operable to remove the top layer from the middle layer. The device can be applied pre-operatively, and then the top layer can be removed post-operatively to remain in place during healing of, for example, an incision site.

32 Claims, 10 Drawing Sheets

(51) Int. Cl.
*A61B 46/20* (2016.01)
*A61B 17/00* (2006.01)
*A61F 13/14* (2006.01)
*A61B 46/00* (2016.01)

(52) U.S. Cl.
CPC ............ *A61B 2017/00951* (2013.01); *A61B 2017/0212* (2013.01); *A61B 2046/205* (2016.02); *A61F 13/148* (2013.01)

(56) References Cited

U.S. PATENT DOCUMENTS

| | | | |
|---|---|---|---|
| 3,826,253 A | 7/1974 | Larsh et al. | |
| 3,859,157 A | 1/1975 | Morgan | |
| 4,169,472 A | 10/1979 | Morris | |
| 4,196,723 A | 4/1980 | Moose, Jr. | |
| 4,432,347 A | 2/1984 | Clavin | |
| 4,619,253 A | 10/1986 | Anhauser et al. | |
| 4,621,619 A | 11/1986 | Sharpe | |
| 4,825,866 A | 5/1989 | Pierce | |
| 4,995,383 A | 2/1991 | Andersson | |
| 5,234,462 A | 8/1993 | Pavletic | |
| 5,259,835 A | 11/1993 | Clark et al. | |
| 5,275,177 A | 1/1994 | Wilk | |
| 5,516,581 A | 5/1996 | Kreckel et al. | |
| 5,599,289 A | 2/1997 | Castellana | |
| 5,611,333 A | 3/1997 | Johnson | |
| 5,672,402 A | 9/1997 | Kreckel et al. | |
| 5,891,077 A | 4/1999 | Gilman et al. | |
| 5,985,395 A | 11/1999 | Comstock et al. | |
| 6,200,195 B1 | 3/2001 | Furuno et al. | |
| 6,350,175 B2 | 2/2002 | Johnson et al. | |
| 6,383,502 B1 | 5/2002 | Dunshee et al. | |
| 6,541,089 B1 | 4/2003 | Hamerski et al. | |
| 6,814,700 B1 | 11/2004 | Mueller et al. | |
| 6,857,935 B1 | 2/2005 | Dohan | |
| 7,066,182 B1 | 6/2006 | Dunshee | |
| 7,122,236 B2 | 10/2006 | Mitchell et al. | |
| 7,374,633 B2 | 5/2008 | Sellars | |
| 7,473,158 B2 | 1/2009 | Horton | |
| 7,637,798 B2 | 12/2009 | Lutzi | |
| 7,938,121 B2 | 5/2011 | McKnight et al. | |
| 9,408,741 B2 | 8/2016 | Blurton et al. | |
| 2002/0191331 A1 | 12/2002 | Nonaka et al. | |
| 2005/0150503 A1 | 7/2005 | Votel | |
| 2006/0137262 A1 | 6/2006 | Crowder-Moore et al. | |
| 2008/0103366 A1 | 5/2008 | Banchieri et al. | |
| 2008/0210223 A1 | 9/2008 | Joines et al. | |
| 2009/0264709 A1 | 10/2009 | Blurton et al. | |
| 2010/0145155 A1 | 6/2010 | Sorajja | |
| 2010/0318013 A1 | 12/2010 | Fabo et al. | |
| 2011/0118646 A1 | 5/2011 | Marcoux et al. | |
| 2011/0250375 A1 | 10/2011 | Bries et al. | |
| 2012/0029295 A1 | 2/2012 | Long Sharps et al. | |
| 2012/0143010 A1 | 6/2012 | Deasey et al. | |
| 2012/0221044 A1* | 8/2012 | Archibald | A61B 17/085 606/214 |
| 2012/0308754 A1 | 12/2012 | Dehlinger et al. | |
| 2012/0312308 A1 | 12/2012 | Allen | |
| 2013/0048203 A1 | 2/2013 | Yau et al. | |
| 2013/0133668 A1 | 5/2013 | Fisher | |
| 2016/0007980 A1 | 1/2016 | Galbierz et al. | |
| 2019/0336233 A1 | 11/2019 | Galbierz et al. | |

FOREIGN PATENT DOCUMENTS

| | | |
|---|---|---|
| EP | 0570317 A1 | 11/1993 |
| EP | 0638301 B1 | 9/1999 |
| EP | 0942940 B1 | 7/2002 |
| EP | 0971661 B1 | 1/2004 |
| EP | 0864311 B1 | 10/2004 |
| EP | 1944001 B2 | 3/2013 |
| WO | 9707760 A1 | 3/1997 |
| WO | 2003043822 A1 | 5/2003 |
| WO | 2014120746 A1 | 8/2014 |
| WO | 20140120746 A1 | 8/2014 |
| WO | 2015052288 A1 | 4/2015 |

OTHER PUBLICATIONS

Written Opinion for corresponding PCT/2017/033593, dated Aug. 22, 2017 mailed.
Extended European Search Report from corresponding EP Application No. 17803333.8 dated Dec. 16, 2019.

* cited by examiner

FIG. 4
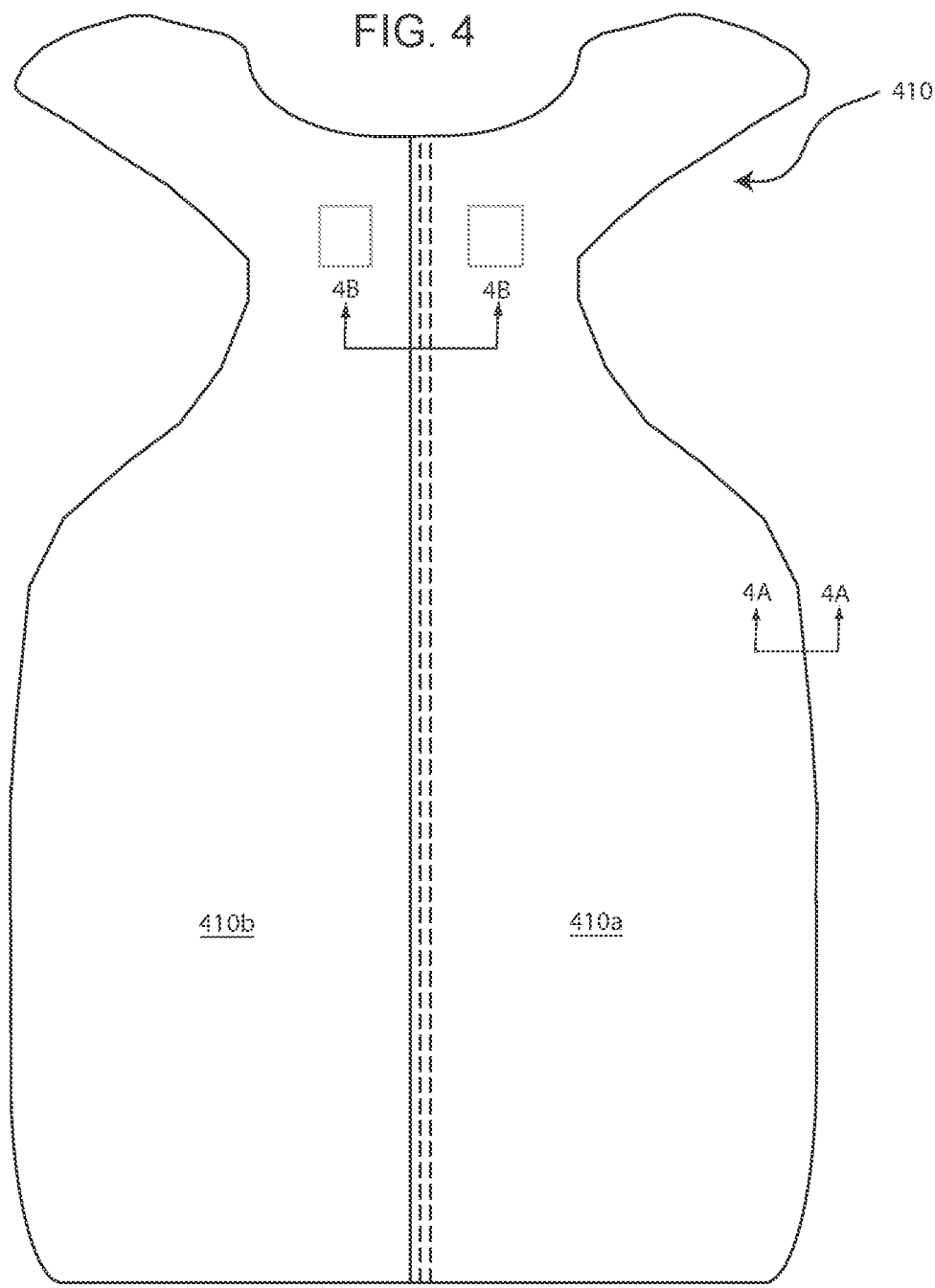
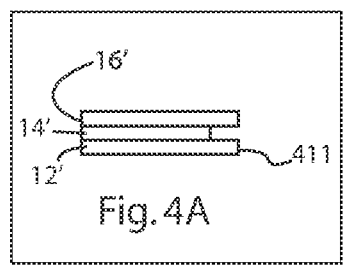
Fig. 4A
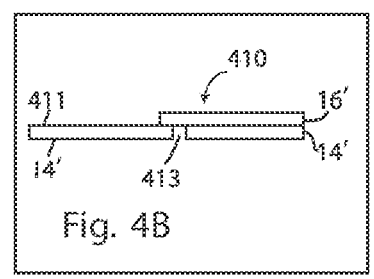
Fig. 4B

3-Ply Extended Liner Tab Details

FIG. 10A
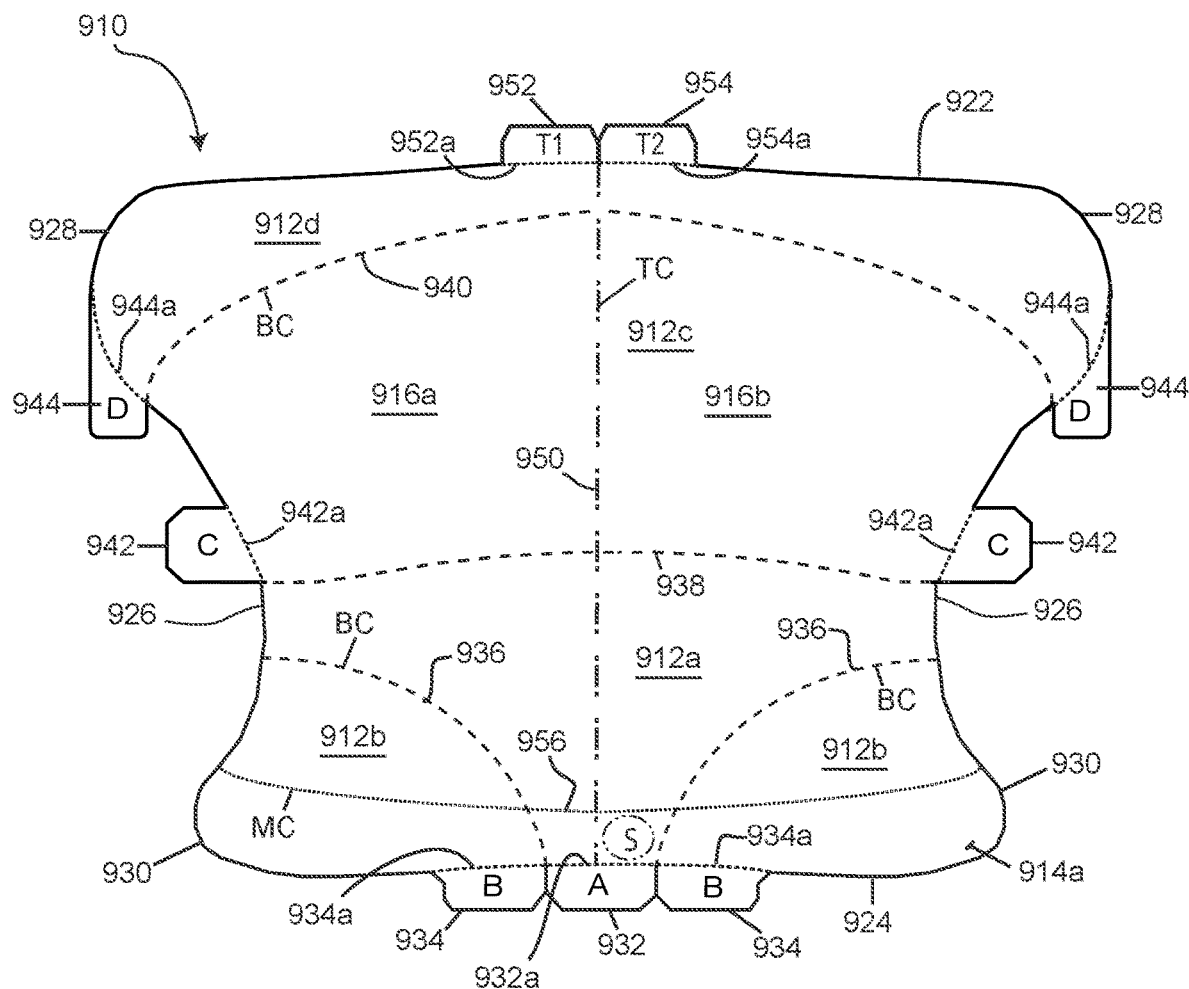
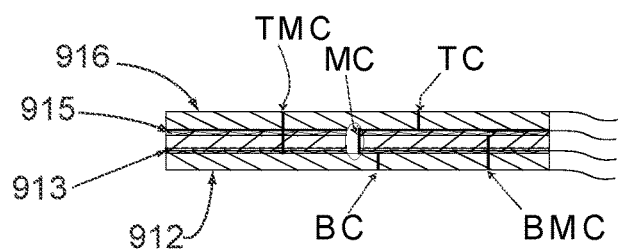
FIG. 10B

MULTI-PLY RETRACTOR/STABILIZER AND WOUND EXPOSURE DEVICE AND METHOD OF USE

CROSS-REFERENCE TO RELATED APPLICATIONS

This application is the US National Stage application of PCT/US2017/033593, filed May 19, 2017, which claims priority to U.S. App. No. 62/341,730 filed May 26, 2016 and entitled "Multi-Ply Retractor/Stabilizer And Wound Exposure Device For Use With Patients Having Excessive And/Or Redundant Tissue And Method Of Use". Additionally, this application is related to U.S. Pat. No. 9,427,222 which is entitled "Retractor/Stabilizer For Excessive And/Or Redundant Tissue And Method Of Use," and to International App. No. PCT/US2016/013404 (published as WO2016/122892) which is entitled "Wound Care Exposure Device For Use With Patients Having Excessive And/Or Redundant Tissue And Method Of Use." All of said patents and applications are incorporated herein by reference.

STATEMENT REGARDING FEDERALLY SPONSORED RESEARCH OR DEVELOPMENT

Not Applicable.

FIELD OF THE INVENTION

This application relates to an engineered, adaptable, predictable supporting device/system that can be used to displace, reposition, retract, secure and/or stabilize excess and/or redundant tissue both during a medical/surgical procedure and for an extended period of time after the procedure to maintain such excess tissue away from a wound (such as a surgical incision) initially to facilitate the procedure and subsequently to facilitate healing of the wound. The excess or redundant tissue can be adipose tissue (such as on the neck, legs, back, sides, etc.), breast tissue, panniculus tissue, etc. The device can be termed a retractor/wound exposure assist device.

BACKGROUND OF THE INVENTION

A significant portion of surgical patients present to the operating room with a BMI (Body Mass Index) over 30. People with a BMI over 30 are considered to be obese, and will commonly have a panniculus (or layer/apron of fat which hangs from the abdomen). Depending on how obese the individual is, the panniculus (or adipose layer or fatty layer) can extend to the pubic hair line (in smaller panniculi) or to the knees and beyond (in very large panniculi). This situation has been arising more frequently in recent years due to a greater number of people being morbidly obese than in years past. Many of these individuals accumulate a large mass of adipose (fatty tissue) in the lower abdominal area producing a panniculus (apron of fat) that hangs, depending on its size, over abdominal wounds, and depending on the size or severity of the panniculus, can hang over the groin, genital area, or upper thighs.

Patients with such large BMIs require the clinical staff to manage excessive amounts of adipose (or fatty tissue), skin and other tissues both during medical procedures (to facilitate the procedure) and after the medical procedure (to facilitate healing of any incisions). In addition to the panniculus, the excess or redundant tissue can also include breast tissue, or adipose tissue in the neck, back, leg, or sides of the patient. In U.S. Pat. No. 9,427,222, which is incorporated herein by reference, we disclose a retractor system which can be used to retain excessive or redundant tissue away from a surgical site. However, the retractor system of U.S. Pat. No. 9,427,222 was initially designed for use during a surgical procedure. In WO2016/122892, which is also incorporated herein by reference, we disclose a wound exposure device that is designed for application after a surgical procedure, and after any retractors that had been used have been removed. As can be appreciated, if a wound exposure device is used that is separate from the retractor, the retractor will need to be removed from the patient and then the wound exposure device applied to the patient. The removal of one device and application of a second device could irritate the patient's skin. Further, application of a second device would require the clinical staff to engage in two retracting procedures—the first, during application of the retractor, and the second during application of the wound exposure device. However, in view of the fact that the retractor disclosed in U.S. Pat. No. 9,427,222 (which is commercially available from GSquared Medical LLC of Brentwood, Tenn. under the name Retentus®) is already applied to the patient, it would be desirable to provide a retractor which can also function as a wound exposure device to retain the adipose tissue in a retracted position after a surgical procedure to facilitate healing of any incisions, punctures or wounds.

SUMMARY

Briefly stated, A multi-ply adhesive device to retract excess or redundant tissue from an incision site on a patient prior to a medical/surgical procedure, and to then maintain the excessive/redundant tissue away from the incision site after the medical/surgical procedure to facilitate healing of the incision site. The device comprises a top layer, a backing layer and a middle layer between the top and backing layers; the middle layer being comprised of at least one middle ply and having a middle layer top surface and a middle layer bottom surface, the at least one middle ply being stretchable. A middle-ply adhesive is applied to substantially the entirety of the middle layer bottom surface to removably adhere the backing layer to the middle layer bottom surface.

The device includes at least one bottom ply tab which is integral with the device. The bottom ply tab comprises an inner edge defined by a cut extending through the top and middle layers such that when the at least one bottom ply tab is pulled away from the top and middle layers, at least a portion of the backing layer will be removed from the middle layer to expose the adhesive of the middle layer.

Additionally, the device includes at least one top ply tab integral with the device. The at least one top ply tab comprises an inner edge defined by a cut extending through the bottom and middle layers such that when the top ply tab is pulled away from the bottom and middle layers, at least a portion of the top layer will be removed from the middle layer.

The device can include any of the following features in any desired combination.

In accordance with an aspect of the device, the middle ply adhesive is a gel adhesive, such as a silicone adhesive or a co-adhesive.

In accordance with an aspect of the device, the top ply is adhered to the middle ply without adhesive.

In accordance with an aspect of the device, the top ply is adhered to the middle ply with a top-ply adhesive which substantially covers a bottom surface of the top ply. This top-ply adhesive can be an acrylate adhesive or a co-adhesive.

In accordance with an aspect of the device, the device can include at least one "press" area at an edge of the device. The "press" area, if provided, is defined by a top cut such that the top ply of the "press" area is not connected to the top ply of the remainder of the body; such that, during use, the "press" area can be pressed against while the top ply tab is used to remove the top ply from the device to reduce the possibility of the middle ply from lifting off a patient during removal of the top ply.

In accordance with an aspect of the device, the back ply is made from a material which is substantially non-stretchable. The back ply can be made from a paper or from an LDPE, PET or poly film In accordance with an aspect of the device, the top and middle layers are polymers, and the middle layer is more stretchable than the top layer. In a preferred embodiment, the top layer is substantially not stretchable and the middle layer is highly stretchable.

In accordance with an aspect of the device, top layer is substantially fluid impermeable.

In accordance with an aspect of the device, the middle layer is air permeable.

In accordance with an aspect of the device, the top ply tab at least partially overlaps the bottom ply tab.

In accordance with an aspect of the device, the device comprises a lower body portion and an upper anchor point portion.

In accordance with an aspect of the device, the backing layer of the body portion has a plurality of back cuts, such that the backing layer defines a plurality of panels. The device includes a bottom ply tab for each of the backing layer panels. Preferably, at least two of the plurality of panels of the backing layer extend have a side-to-side width which, at least in part, is equal to the side-to-side width of the device.

In accordance with an aspect of the device, the device includes stretch features which allow the device to be stretched during application of the device to a patient before removal to the top layer of the device. The stretch feature includes a perforated line which extends through just the top layer and extends the width of the device. The perforated line divides the top layer of the device into a top layer lower portion and a top layer upper portion. The perforated line can be broken by pulling the upper portion of the device away from the lower portion to enable the middle layer of the device to be selectively stretched during application of the device to a patient. In this embodiment, the at least one top layer tab includes a first top layer tab associated with the top layer below the perforated line and a second top layer tab associated with the top layer above the perforated line. This embodiment of the device can be provided with a tension gauge for measuring the amount of tension applied to the device when the middle layer is pulled. In one example, the tension gauge comprises a tongue extending from the top ply lower portion into the top ply upper portion and tension indicia on the top ply upper layer adjacent the tongue; the indicia indicating the amount of tension applied to the middle layer.

In accordance with another aspect of the device, the device is formed from a single piece of multi-ply material.

In accordance with an aspect of the device, the device is formed from at least a first and a second piece of material. In an illustrative embodiment, the device is formed from a bottom section, a mid-section, and a top section which are joined together, wherein at least the mid-section is formed from a material which is different than the material from which the top and bottom sections are formed. The top and bottom sections can be formed from the same material or from different materials. The mid-section, in this embodiment, can be void of adhesive on the bottom surface of the mid-section.

In accordance with an aspect of the device, the device includes at least one top cut which divides the top ply into at least two top ply panels, and wherein the device further includes a top-ply tab associated with each top ply panel to remove the top-ply panels from the middle ply.

In accordance with an aspect of the device, the device includes a middle ply cut which extends only through the middle ply. Preferably, the middle ply cut extends across the device proximate the bottom edge of the device.

In accordance with an aspect of the device, the device includes at least one indicator/sensor adapted to monitor a parameter chosen from the group consisting of elongation and/or stretch of the retractor/stabilizer, and ambient and physiological aspects of the patient's wound. The indicator/sensor is adapted to indicate if the monitored parameter exceeds or falls below a predetermined threshold. If the indicator/sensor monitors elongation/stretch of the retractor/stabilizer, the indicator/sensor can be a mechanical indicator incorporated into the retractor/stabilizer. Regardless of the parameter being monitored, the indicator/sensor can transmit to a receiver a signal indicative of the parameter being monitored. Such transmission can be wireless or via direct electrical connection.

BRIEF DESCRIPTION OF THE SEVERAL VIEWS OF THE DRAWINGS

FIG. 4 shows a plan view of alternative 2-piece retractor/wound exposure device, wherein the two pieces are mirror images of each other and cooperate to form a complete retractor/wound exposure device;

FIG. 4A is a representative cross-sectional view of one of the pieces of the device taken along line 4A-4A of FIG. 4;

FIG. 4B is a cross-sectional view taken along line 4B-4B of FIG. 4, but with the backing removed from both pieces of the device, and the top ply removed from the left side piece of the device;

FIG. 10A is a plan view of a further illustrative embodiment of the device;

FIG. 10B is a schematic cross-sectional view of the device of FIG. 10, showing the plies of the device and the various cuts used in manufacturing the device.

Corresponding reference numerals will be used throughout the several figures of the drawings.

DETAILED DESCRIPTION

Figure 1:
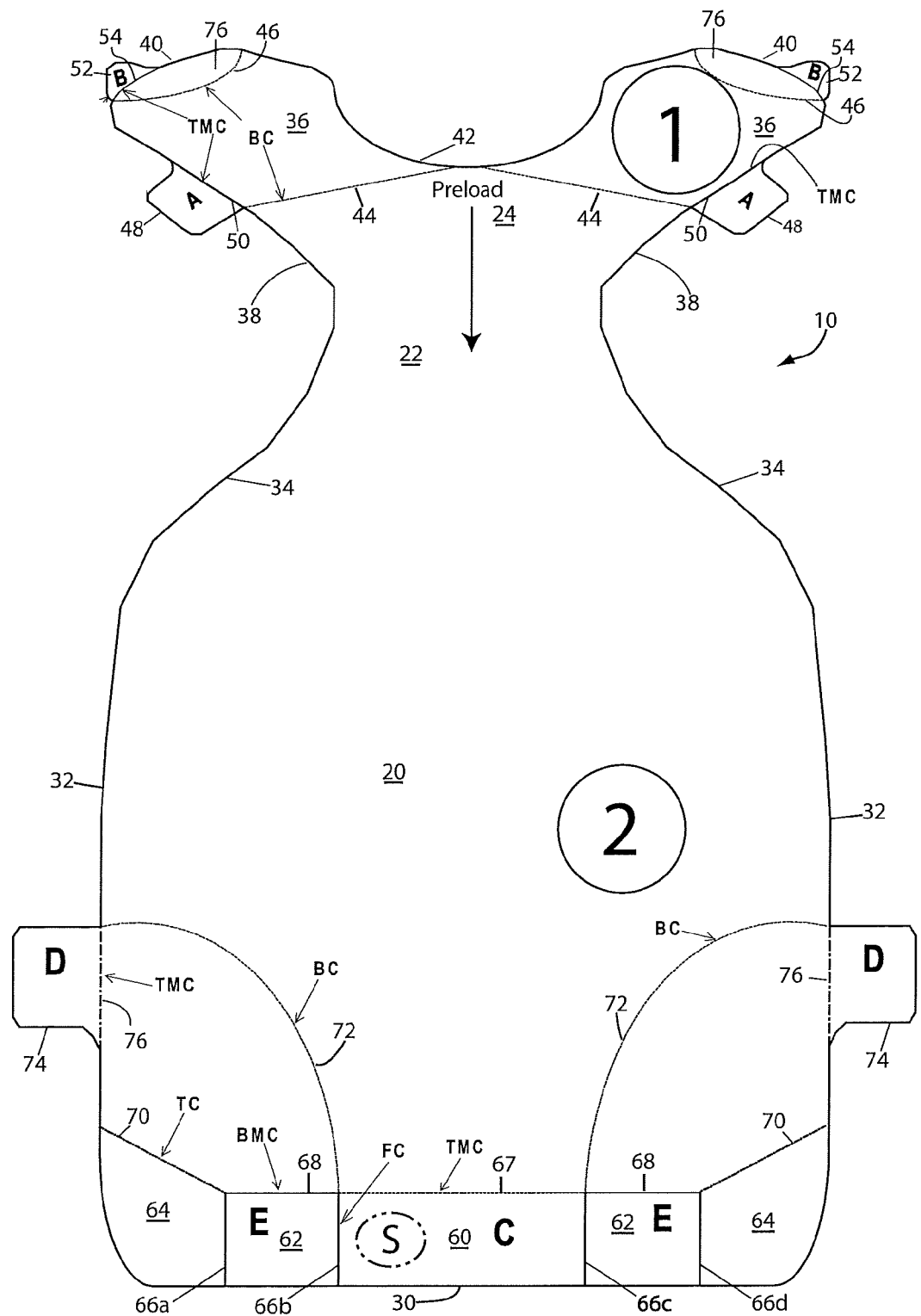
FIG. 1 is a plan view of a first illustrative retractor/wound exposure device.

The following detailed description illustrates the claimed invention by way of example and not by way of limitation. This description will clearly enable one skilled in the art to make and use the claimed invention, and describes several embodiments, adaptations, variations, alternatives and uses of the claimed invention, including what we presently believe is the best mode of carrying out the claimed invention. Additionally, it is to be understood that the claimed invention is not limited in its application to the details of construction and the arrangements of components set forth in the following description or illustrated in the drawings. The claimed invention is capable of other embodiments and of being practiced or being carried out in various ways. Also, it is to be understood that the phraseology and terminology used herein is for the purpose of description and should not be regarded as limiting.

Figure 2:
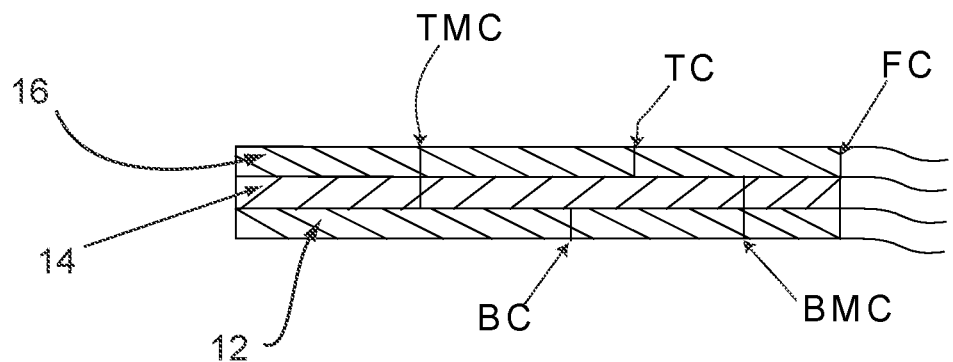
FIG. 2 is a representative cross-sectional view of the device on an enlarged scale.

A first illustrative embodiment of a retractor/wound exposure device 10 is shown in FIG. 1. As will be described below, the retractor/wound exposure device 10 can be used to retract excessive tissue away from a surgical site, and to restrain, secure, hold, etc. the excessive tissue away from a wound (such as a surgical incision) to facilitate healing of the wound after the surgical/medical procedure is complete. As noted above, such excessive and/or redundant tissue can a panniculus, or adipose tissue in the neck, back, leg, or sides of the patient. The device 10 is formed from a multi-ply (preferably at least 3-ply) material, such as by die-cutting. A representative cross-section of the material is shown on a grossly enlarged scale in FIG. 2. As seen therein, the material includes a bottom ply or layer 12, a middle ply or layer 14, and a top ply or layer 16. The middle layer is shown in the Figure to be one ply; however, the middle layer could comprise two or more plies. The device 10, as noted, can be formed by die-cutting, and thus the device, in an as-supplied form, includes (1) top cuts TC which extend only through the top ply 16; (2) top-middle cuts TMC which extend through the top and middle plies, but which do not extend through the bottom ply; (3) full cuts FC which extend through all the plies; (4) bottom cuts BC which extend only through the bottom ply; and (5) bottom-middle cuts BMC which extend through the bottom and middle plies 12, 14, but do not extend through the top ply 16. The purpose for the different cuts will become apparent from the description below. Although the various cuts are preferably continuous, the cuts can instead be perforations. Thus, as used herein, a "cut" is defined to include a perforated cut.

The bottom ply 12 is preferably a release liner, and can be made, for example, of a substantially non-stretchable material, such as Kraft paper. The liner can also be a PET or other polymer film. The middle ply 14 is preferably a material that is stretchable, and preferably, substantially stretchable, in at least one direction. The middle ply could, for example, be a polymer film, or could be a material that has an elastic component, such as Spandex® The top ply 16 is preferably made from a polymer film different from the middle ply and which has at best only slight stretchability. The middle ply has a lower surface coated with a hypoallergenic pressure sensitive adhesive (such as an acrylic, acrylate, or silicone adhesive) to removably secure the bottom ply release liner 12 to the middle ply 14. The top ply 16 is adhered to the middle ply 14 without the use of an adhesive. For example, the top ply 16 can self-adhere to the middle ply 14 by means of co-adhesion. A preferred material for the retractor/wound care device 10 is 3M 9836 medical tape (available from 3M). In this tape, the bottom ply 12 is comprised of a non-stretchable silicone coated paper, which is, for example, about 5 mil (about 0.127 mm) thick. The middle ply 14 is a polyethylene film having an acrylic adhesive applied to a bottom side thereof, to removably secure the bottom ply to the middle ply. The middle ply is highly conformable and is stretchable, having a percentage of elongation/stretchability of approximately 5%-500%. Additionally, this middle ply is typically breathable, and preferably has a high vapor transmission rate (VTR), from about 500 to about 8000 g/m$^2$/24 hrs. The middle ply can have a thickness of about 1 mil (about 0.03 mm). The top ply can be a polyolefin film with a thickness of about 2.5 mil (about 0.06 mm). The top ply can be slightly stretchable, but in any event has a stretchability less than the stretchability of the middle ply. For example, the top ply can have a low to moderate elongation/stretchability percentage, such as from zero to about 500%. As such, the top ply can be substantially non-stretchable. The top ply is liquid impermeable, and is also preferably air impermeable. The overall device as-supplied (liner ply, middle ply, and top ply) has a thickness of about 7.5 mil (about 0.2 mm). When the bottom (liner) layer 12 is still adhered to the middle ply 14, the device is substantially not stretchable.

Turning back to FIG. 1, the device 10 includes main body section 20, a neck section 22 and a yoke section 24. The main body is shown to be generally rectangular, but, as noted in some of the other embodiments, can be differently shaped to conform to the procedure/application and body shape of the patient. The body 20 has a bottom edge 30 and side edges 32. The bottom edge is shown to be flat, but could be concave or convex to conform better to the natural curvature of the body. The neck section 22 is a reduced width area of the device 10, and is defined by side edges 34 which curve or slope inwardly and upwardly from the upper ends of the body side edges 32. The yoke 24 comprises a pair of arms 36 which extend diagonally outwardly from the top of the neck section 22. The arms 36 are defined by lower edges 38 which extend outwardly from the neck edges 34. The lower edges 38 curve around to upper edges 40 of the arms, and the two upper edges 40 are joined by a concave U-shaped upper edge 42.

As described below, the device 10 is provided with a plurality of bottom ply tabs 30, 48, 74a which enable the paper ply 12 to be removed from the middle ply 14 in several pieces to thereby expose the adhesive of the middle ply for application of the device 10 to a patient. In addition, the device includes top ply tabs 62 to enable removal of the top ply 16 from the middle ply 14 after application of the device 10 to a patient.

The yoke 24 includes a back cut 44 which extends at a slight cant from the center of the U-shaped edge 42 toward the yoke edges 38. Additional concave bottom cuts (BC) 46 at the ends of the arms 36 have opposite ends along the yoke upper edge 40. An A-tab 48 extends outwardly from each yoke edge 38, and is defined in part by an inner top-middle cut 50 which is co-linear with the yoke edge 38. Additionally, a B-tab 52 extends from each top edge 40 of the yoke between the ends of the top-middle cuts 46. The inner edges of the B-tabs 52 are defined by top-middle cuts 54. As such, the A- and B-tabs are bottom ply tabs which remove their associated portions of the bottom ply or liner from the middle ply.

The device 10 includes a series of cuts along the bottom edge of the body 20 that form five sections/tabs as follows: a center bottom ply C-tab 60, two top ply E-tabs 62a,b, and two outer finger press areas 64. These tabs/sections are defined by four full cuts 66a-d which extend upwardly generally perpendicularly from the bottom edge 30 of the body 20. The full cuts fully separate the tabs 60, 62a,b and sections 64a,b from each other. The top edge of the middle or C-tab 60 is defined by a top-middle cut (TMC) 67 which extends generally parallel to the bottom edge 30 and between the full cuts 66b and 66c. The top edge of the E-tabs 62 are defined by bottom-middle cuts (BMC) 68 which extend between the full cuts 66a and 66b on one side of the device and 66c and 66d on the other side of the device. Finally, top cuts (TC) 70 extend diagonally downwardly from the side edges 32 of the body 10 to the top ends of the full cuts 66a and 66d to define top edges of the finger press areas 64 of the body 20. In addition, large arced bottom cuts (BC) 72 extend from the tops of the full cuts 66b,c to the edges 32 of the body 20 to define bottom corner panels of the bottom ply. Finally, bottom ply D-tabs 74 extend outwardly from the side edges 32, with the top edges of the tabs 74 being level with or below the point where the bottom cuts 72 intersect the side edges 32. The inner edges of the tabs 74 are defined by top-middle cuts (TMC) 76 which are co-linear with the side edge 32 of the body 20.

The inner edges of the A-, B-, C- and D-tabs 48, 52, 60, and 74, respectively, are defined by top-middle (TMC) cuts, so that the top and middle plies of the tabs are separated from the top and middle plies of the rest of the device. Thus, when these tabs are pulled, they will pull the backing or bottom ply 12 away from the middle ply 14 to expose the adhesive on the middle ply. Hence, they are, as noted, bottom ply tabs. The inner edge of the E-tabs 62 are defined by bottom-middle cuts 68, and thus separate the bottom and middle plies on the tabs from the bottom and middle plies of the rest of the device. Therefore, when the E-tabs 62 are pulled, they will lift the top ply 16 off of the middle ply 14. Hence, the E-tabs, as noted, are top ply tabs.

The A-E tabs define two types of tabs. The A-tabs 48, B-tabs 52, and the D-tabs 74 extend from the edge of the device, and are thus considered outboard tabs. The C-tab 60 and E-tabs 68, on the other hand, have outer edges which are commensurate, flush, or even with the edge of the device. That is, they do not protrude from the edge of the device as do the A-, B- and D-tabs. The C- and E-tabs are thus considered inboard tabs. The device could be formed with all the tabs being inboard tabs, all the tabs being outboard tabs, or with both inboard and outboard tabs, as shown. In this latter instance, any selected group of the A-E tabs could be inboard tabs, and the remaining tabs would then be outboard tabs.

To apply the device 10 to a patient, the patient is preferably supine. The A-tabs 48 are initially pulled to peel the backing layer 12 from the yoke 24 (except in the area defined by the cut lines 46) to expose the adhesive of the middle ply 14 of the yoke. The area defined by the cuts 46 thus define gripping or hold areas 76 for the yoke. When the backing of the yoke is removed by pulling the A-tabs, the backing remains in the hand hold areas 76. The yoke is then adhered to an anchor point on the patient to position the device 10 on the patient. When retracting the panniculus, this anchor point is preferably between the patient's upper thorax and xiphoid process. Staff can grip the yoke by the hold areas 76, so that they can handle the yoke without contacting the adhesive in the areas defined by the cuts 46. Once the yoke area has been positioned and adhered to the patient, the staff will manually retract the patient's panniculus toward to the anchor point (in a panniculus retraction, this is a cephalad direction). While holding the panniculus in the retracted position, other staff will hold the device 10 in the corner areas (defined by the cuts 72) and pull the bottom C-tab 60 to remove the bottom ply 12 from the device body 20 (except for the bottom corner panel of the bottom ply defined by the cuts 72) and from the neck 22 to expose the adhesive of the middle ply in the neck and majority of the body. While holding the panniculus in the retracted position, the body 20 and neck 22 of the device 10 are adhered to the patient and smoothed out. Once the body 20 and neck 22 have been adhered to the patient's panniculus, the device 10 will hold the panniculus in the desired retracted position. Staff can thus stop manual retraction of the panniculus. As a last step, staff will remove the backing layer in the bottom corners by pulling on the D-tabs 74. The D-tabs will remove the backing layer from the bottom corners of the body except for the backing of the E-tabs 62. Thus, staff can hold the E-tabs 62 to facilitate removal of the backing in the bottom corners of the body. The corner areas of the body can then be smoothed out over the patient. As can be appreciated, at this point in the application process, the backing layer 12 has been removed from the device except for in the E-tabs and the gripping areas 76. If desired, the B-tabs can be pulled to remove the backing ply from the finger grips 76 at any time after the yoke 24 has been adhered to the patient to adhere the top portion of the yoke to the patient.

With the device 10 now applied to the patient, the patient will have the middle ply 14 and top ply 16 covering the panniculus and holding the panniculus in the retracted position. The top ply 16, as noted above, has little to no stretchability, and thus, the top ply will prevent the panniculus from falling back to a relaxed position. With the panniculus held securely in a retracted position, the medical staff can proceed with the procedure or operation to be performed on the patient. The application process was described with respect to retraction of a patient's panniculus. As noted above, the device can also be used to retract breast tissue or excess adipose tissue in virtually any other part of the body. Application of the device to retract breast tissue or other adipose tissue will be substantially the same as described above. However, as can be appreciated, the anchor point will vary with the area of the tissue to be retracted.

Although the device 10 was described as being applied from the top (yoke) down to the bottom (body), the device 10 could be applied by initially adhering the body 20 to the patient after manual retraction of the panniculus in a cephalad direction, much as described in the above-noted U.S. Pat. No. 9,427,222. When retracting a panniculus, once the body 20 is adhered to the panniculus, the device 10 is pulled toward the anchor point (i.e., in a cephalad direction) to maintain the retraction of the device, and is then adhered to the anchor point, i.e., between the patient's upper thorax and xiphoid process. As can be appreciated, the ability of the device 10 to support the panniculus (or other excess flesh)

out of the way of the incision site can enable orthopedic surgeons to perform surgery on higher BMI patients with an anterior approach.

After the procedure has been completed, the patient may have a suture wound or puncture wound which will need to heal. It is thus desirable to maintain the retracted tissue in the retracted position, to facilitate healing of the wound. Because the top ply is relatively thick (i.e., about 2.5 mils) and is a non-breathable film (i.e., not air permeable), it is not ideal for long term wear. By pulling upwardly on the top-ply E-tabs 62, the top ply 16 will be removed from the middle ply 14, so that only the middle ply remains on the patient. The adhesive which holds the middle ply to the patient is relatively weak. Thus, the action of pulling the top ply 16 from the middle ply 14 can cause the middle ply to separate or be pulled from the patient's skin. To prevent this from happening, staff can press down on the corner finger press areas 64 to hold the corners of the middle ply in place, and then pull up on the E-tabs 62 to separate the top ply 16 from the middle ply 14. If staff do not press down in the corner tabs 64, there is a risk that pulling up on the E-tabs would start separating the middle ply from the patient's skin. With the top ply 16 removed, all that remains on the patient is the middle ply 14. As noted above, the middle ply is breathable (i.e., at least air permeable if not also liquid permeable), stretchable, highly conformable, and thin (about 1 mil thick). It is thus more comfortable for the patient to wear long term (i.e., several days or even weeks). The device can thus remain on the patient while the wound heals. Although the middle ply 14 is highly stretchable, it will maintain the panniculus off the wound site, so that the wound is exposed to ambient atmosphere to facilitate healing. Otherwise the panniculus could cover the wound which would hinder healing and potentially result in an infection at the site of the wound.

Once the wound has healed, the remaining middle ply can be removed from the patient. As noted above, the adhesive is a relatively weak adhesive, and by carefully lifting the middle ply from the patient, the remaining middle ply can be removed without substantial trauma to the patient's skin.

Application of the retractor/wound exposure device is described above as being initially applied to the patient pre-operatively. Post operatively, the top ply is then removed. However, in certain circumstances, it may be desirable to apply the device to a patient post-operatively. In this instance, the device is applied as described above. The top ply may be allowed to remain in place for a desired period of time, if the reduced stretchability of the top ply is desired. Alternatively, the top ply can be removed promptly as part of the application process.

The retractor/wound exposure device 10 is a basic device. Various features, described below, can be added to the device in any combination to facilitate application of the device to the patient or to take advantage of the stretchability of the middle ply 14 during application of the device to the patient.

Figure 3:
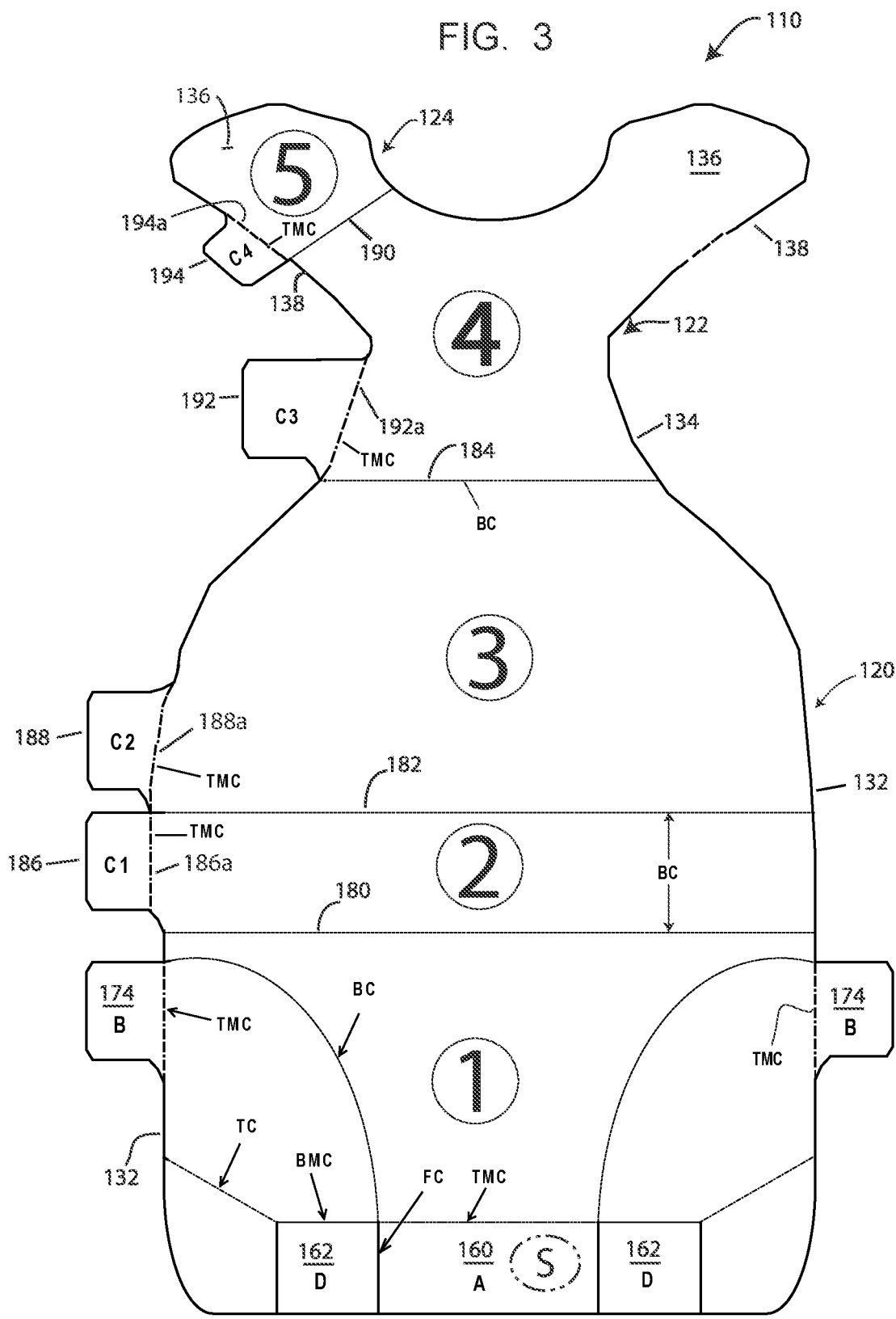
FIG. 3 is a plan view of a variation of the retractor/wound exposure device of FIG. 1 which allows for removal of a backing layer in multiple sections, and thus allows for incremental application of the device to a patient.

FIG. 3 shows a retractor/wound exposure device 110 which is substantially similar to the device 10 of FIG. 1; however, it is designed to remove the backing ply 12 from the device, and especially the device body 120 in multiple sections, to facilitate application of the device to the patient. Additionally, rather than being applied top down, the device 110 is intended to be applied bottom up (i.e., the body 120 is applied to the patient first, and then the device is anchored to the patient between the patient's xiphoid process and upper thorax as describe in our above noted WO2014/120746).

The bottom third of the device 110 is substantially identical to the bottom third of the device 10, and will not be further explained. However, it is noted that in the device 110, the bottom ply tab 160 is an A-tab, the top ply tabs 162 are D-tabs, and the bottom ply tabs 174 are B-tabs.

The device 110 includes a pair of spaced apart (and generally parallel) back cuts (BC) 180 and 182 which extend across the body 120, with the lower back cut 180 being slightly above the B-tabs 174 and the back cut 182 being slightly above the back cut 180. A third back cut 184 extends across the top of the body 120 just below the neck 122. A bottom ply tab 186 (labeled C1) extends from the body edge 132 between the back cuts 180 and 182. The inner edge of the tab 186 is defined by a top-middle cut 186*a*, such that when the C1-tab 186 is pulled, it will remove the backing layer from the middle ply between the cuts 180 and 182. Thus, the C1 tab will remove a strip of the backing layer. A further bottom ply tab 188 (labeled C2) extends from the body edge 132 above the back cut 182. The inner edge of the tab 188 is defined by a top-middle cut 188*a*, such that when the C2-tab 188 is pulled, it will remove the backing layer from the middle ply between the back cuts 182 and 184. Hence, the backing ply 12 in the body 120 is removed using the A-tab 160, the B-tabs 174, the C1-tab 186, and the C2-tab 188. As with the device 10, these tabs leave the backing layer of the D-tabs 162 in place when the backing is removed from the body 120.

The yoke 124 is substantially identical in shape to the yoke 24 of the device 10; however, the tabs in the neck 122 and yoke 124 of the device 110 are altered relative to the device 10. In the device 110, the yoke 124 is provided with a back cut 190 which is generally perpendicular to the bottom edge 138 of the yoke arm and which extends across one of the yoke arms 136 to divide the backing layer of the yoke into at least two portions. A bottom ply tab 192 (labeled C3) extends from the edge 134 of the neck 122 above the back cut 184. The inner edge of the tab 192 is defined by a top-middle cut 192*a*, such that when the C3-tab 192 is pulled, it will remove the backing layer from the middle ply between the cuts 184 and 190. A bottom ply tab 194 (labeled C4) extends from the edge 138 of the yoke arm 136 at or above the cut line 190. The inner edge of the tab 194 is defined by a top-middle cut 194*a*, such that when the C4-tab 194 is pulled, it will remove the backing layer from the middle ply of the arm 136 above the cut 190. Thus, the backing ply of the neck and yoke are removed from the middle ply using the C3- and C4-tabs 192 and 194. The C3-tab 192 removes the backing layer from the neck 122 and yoke 124 (except for the upper portion of one of the yoke arms 136); and the C4-tab 194 removes the backing ply from the upper portion of the yoke arm. The device 110 is shown with a C4-tab 194 on only one yoke arm 136. If desired, the other yoke arm could be provided with a back cut corresponding to the back cut 190 and a second C4-tab, such that the backing ply for the upper portions of both yoke arms is removed independently of the backing ply for the neck and lower portion of the yoke.

As noted above, the retractor/wound exposure device 110 is intended to be applied to the patient starting with the body 120, rather than the yoke, of the device. The provision of the 01- and C2-tabs 186 and 188 allow for the device body 120 to be applied to the patient in essentially three sections (labeled as ①, ②, and ③ in FIG. 3). This allows for the device 110 to be used during the retraction of the panniculus as the device 110 is applied to the patient. Thus, in practice, with the panniculus manually, and at least partially, retracted in a cephalad direction, the A-tab 160 is pulled to remove the backing ply from the middle layer in the area labeled ① in FIG. 3. As seen in FIG. 3, the area ① is generally T-shaped. Once the exposed area of the device in the area ① has been applied to the patient, the B-tabs 174 can be pulled to expose the adhesive of the middle layer in the rest of the body bottom, except for in the D-tabs 162. With the backing layer of the body corner areas removed, the corners of the device 110 can be smoothed out and adhered to the patient's panniculus. With the device 110 now applied to the panniculus, the medical staff can use the device 110 to hold the panniculus in a retracted position. This would still be a manual retraction, because the device yoke has not been anchored to the patient yet. The staff can then pull the C1-tab 186 to remove the strip of the backing layer between the cut lines 180 and 182, which is labeled as area ② in FIG. 3. The medical staff can hold the device 110 such that the exposed adhesive in the area ② is above (i.e., not in contact with) the patient, pull the device in a cephalad direction and manually gather up more of the panniculus under the device 110 in the area ②. With the panniculus now more retracted, the medical staff can adhere the device 110 to the patent in the area ② of the device. Lastly, the medical staff can pull the C2-tab 188 to remove the backing layer from the rest of the body (the area labeled ③ in FIG. 3). The just described steps can then be repeated to further retract the panniculus and finish adhering the body 120 of the device 110 to the patient. Because the top ply 16 and bottom ply 12 are both not stretchable or are both substantially not stretchable, the device 110 will not stretch during application of the device 110 to the patent, and thus can effectively be used, as described, to facilitate the process of retracting the panniculus. This reduces the need for medical staff to hold the panniculus in the retracted position with their hands while the device is being applied, and allows for the device itself to be used to move the panniculus to the retracted position. Although the body 120 is shown as having three major sections (areas ①, ②, and ③), it could have only two sections or it could have more sections, and the size of the sections can be changed as desired.

Once the body 120 has been applied to the panniculus, the medical staff can pull the C3-tab 192 to expose the adhesive of the middle ply in the neck 122 and at least the lower portion of the yoke 124. With the panniculus still being held in the retracted position, the neck and at least the lower portion of the yoke are adhered to the patient between the patient's xiphoid process and an upper portion of the patient's thorax to anchor the device 110 to the patient. At this point, the device 110 will be self-supporting and will support and hold the panniculus in the retracted position. Lastly, the C4-tab 194 can be pulled to expose the adhesive in the upper portion of the arm having the tab (or in both arms if the device is provided with two C4-tabs), and the last, upper portion of the yoke can be adhered to the patient.

After the medical/surgical procedure has been completed, the top ply can be removed from the middle ply in the same manner as described above in conjunction with device 10 by pulling the D-tabs 162.

Figure 6A:
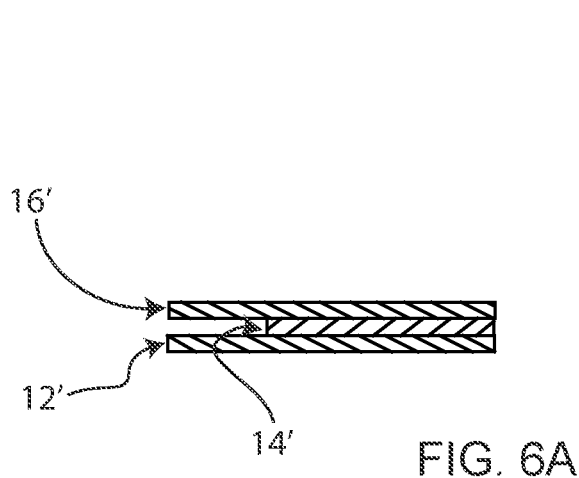
FIG. 6A-6B are cross-sectional and fragmentary plan views of further tab configurations made from a material wherein the top and bottom plies are extended relative to the middle ply.
Figure 6B:
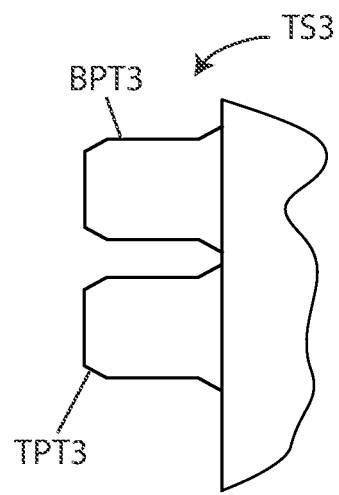

FIG. 4 shows an alternative two-piece retractor/wound exposure device 410 in which the device includes (with reference to FIG. 4) a right hand side 410a and a left hand side 410b which are substantially mirror images of each other and are effectively joined along a vertical midline of the device 410. In the device 410, the material from which the device is made is from a material with an extended liner 411 wherein the middle ply 14' is offset relative to the bottom ply 12' and top ply 16', as seen in FIG. 6A. Stated differently, the top and bottom plies extend beyond the edge of the middle ply. The extension of the bottom ply 12' and top ply 16' relative to the middle ply 14' allows for removal of the bottom and top plies from the middle ply without the need for any tabs.

The device 410 (FIG. 4) is formed of two pieces 410a,b which are mirror images of each other, and in combination, define a two-piece device 410 having substantially the same configuration as the device 10 or 110. In the device 410, the offset edge 411 of the two pieces forms an axis of symmetry for the device 410, and the two pieces are applied to the patient such that the edge of the top plies of the two parts 410a,b are substantially abutting each other. As can be seen in FIG. 4B, when the two pieces 410a,b are applied to the patient, the edges of the top ply 16' will overlay the bottom ply 14', and there will be a slight gap 413 between the middle plies 14' of the two parts 410a,b.

Figure 5A:
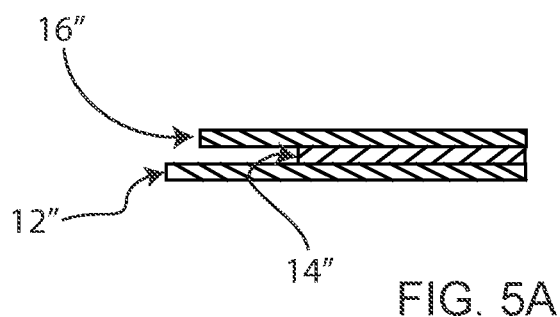
FIG. 5A-5C are cross-sectional and fragmentary plan views of alternate tab configurations each made from a material wherein the top and bottom plies are extended relative to the middle ply.
Figure 5B:
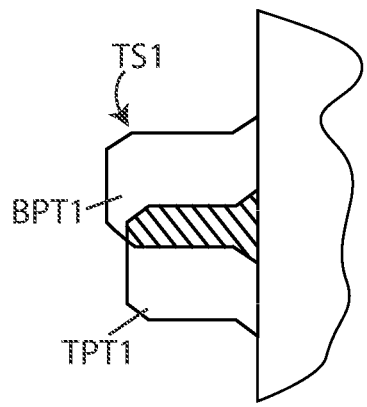

In the devices 10, 110, the tabs which remove the bottom or backing ply do not overlap the tabs which remove the top ply (that is, they are spaced apart on the device). This requires additional space. In material in which the top and bottom plies extend relative to the middle ply, the tabs can overlap. FIG. 5A shows an edge of a material formed so that both the top ply 16" and the bottom ply 12" extend beyond the middle ply 14", and with the extension of the bottom ply 12" beyond the middle ply being greater than the extension of the top ply 16". FIG. 5B shows a first tab style TS1 that can be formed from the material of FIG. 5A. In tab style TS1, the bottom ply tab BPT1 is longer than the top ply tab TPT1, and the top ply tab TPT1 overlies in part the bottom ply tab BPT1. The partial offset and differences in length of the tabs BPT1 and TPT1 enable the bottom ply tab BPT1 to be gripped without gripping the top ply tab TPT1, so that the bottom ply can be removed from the middle layer.

Figure 5C:
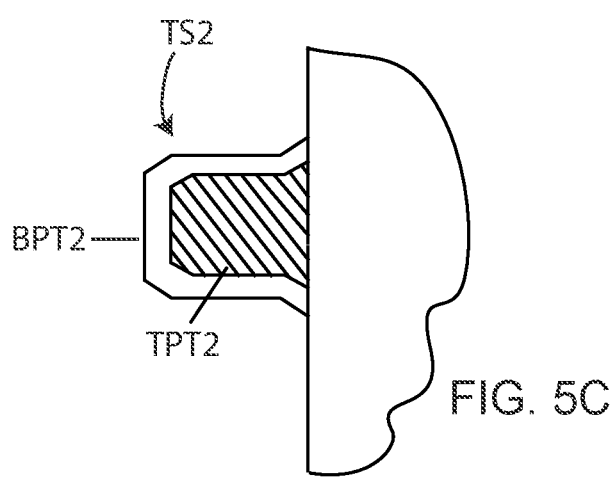

FIG. 5C shows a tab style TS2 in which the top ply tab TPT2 fully overlies the bottom ply tab BPT2, and the bottom ply tab extends beyond the end of the top ply tab. In tab style TS1 (FIG. 5B), the top and bottom ply tabs can be made to have the same width. However, in tab style TS2 (FIG. 5C) where the tabs overlay each other, to facilitate grasping the bottom ply tab BPT2 without grasping the top ply tab TPT2, the bottom ply tab BPT2 is larger in all dimensions than the top ply tab TBT2, as seen in FIG. 5C.

FIG. 6A is substantially similar to FIG. 5A, and shows the top ply 16' and bottom ply 12' extending equidistantly beyond the edge of the middle ply 14'. In this material, a tab style TS3 can be formed in which the bottom ply tab BPT3 is adjacent the TPT3. The bottom and top ply tabs BPT3 and TPT3 could also overlap each other, as in FIG. 5B. In either case, the separation or overlap of the tabs in tabs style TS3 allows for gripping of the bottom ply tab BPT3 without gripping the top ply tab TPT3 to facilitate removal of the bottom ply from the middle ply for application of the device to a patient.

The tab styles TS1-TS3 allow for the tabs to be smaller than the tabs of the devices 10 and 110, and allow for a plurality of tabs to occupy a smaller length along an edge of the device. In addition, because the tabs are formed from the extended portion of the top and bottom plies (i.e., the portion of the top and bottom plies extending beyond the edge of the middle ply), top-middle cuts or bottom-middle cuts (as described in FIG. 2) are not needed to define the inner edges of the tabs. As formed, the tabs (i.e., the portion gripped by the clinician) comprise only the ply to be removed.

The device 610 (FIG. 7) discloses a retractor/wound exposure device that is shaped differently from the devices 10 and 110. However, the overall principle is the same. The device 610 is provided with a transverse back cut 680 which defines an upwardly curving arc. The back cut 680 divides the backing ply of the device into upper and lower sections. The lower section is connected to the A- and B-tabs (bottom ply tabs) located at the bottom edge of the body 620 to remove the backing ply from the device up to the back cut 680. The device 610 is further provided with perforated line 682 formed only in the top ply which is located above the back cut 680. The perforated line 682, as shown, defines an upwardly curving arc, and is provided with a rectangular, upwardly extending tongue 683. The perforated line 682 is shown to be generally parallel to the back cut line 680. The body 620 includes a tension gauge indicia 685 on the body to one side of the tongue 683. The bottom portion of the device 610 is applied to a patient similarly to the device 110. That is, the backing panel associated with the A-tab is removed first, and the middle section of the bottom portion of the middle ply is adhered to the patient's manually retracted panniculus. The side panels of the bottom portion associated with the B-tabs are then removed and the remainder of the bottom portion of the device 610 is adhered to the patient. With the device adhered to the patient by the bottom third of the device, the upper portion can be pulled to break the perforated line 682/683 in the top ply. This will allow the upper portion of the device (which can still include all three plies) to be pulled away from the lower portion of the device to stretch the device. As the upper portion is pulled away from the lower portion, the gauge 685 will move relative to the tongue 683. The amount of pull or preload exerted by the stretched device can be determined by the specific indicia marker that is lined up with the end of the tongue 683. Thus, for example, in FIG. 7, dotted lines schematically show the device stretched such that the device will exert between 5 lbs and 10 lbs of pull when adhered to the patient. As can be appreciated, the gauge is calibrated to show the amount of pull exerted when the middle ply is stretched to varying degrees. Any of the retractor/wound exposure devices disclosed herein could be provided with a similar gauge if desired.

Figure 7:
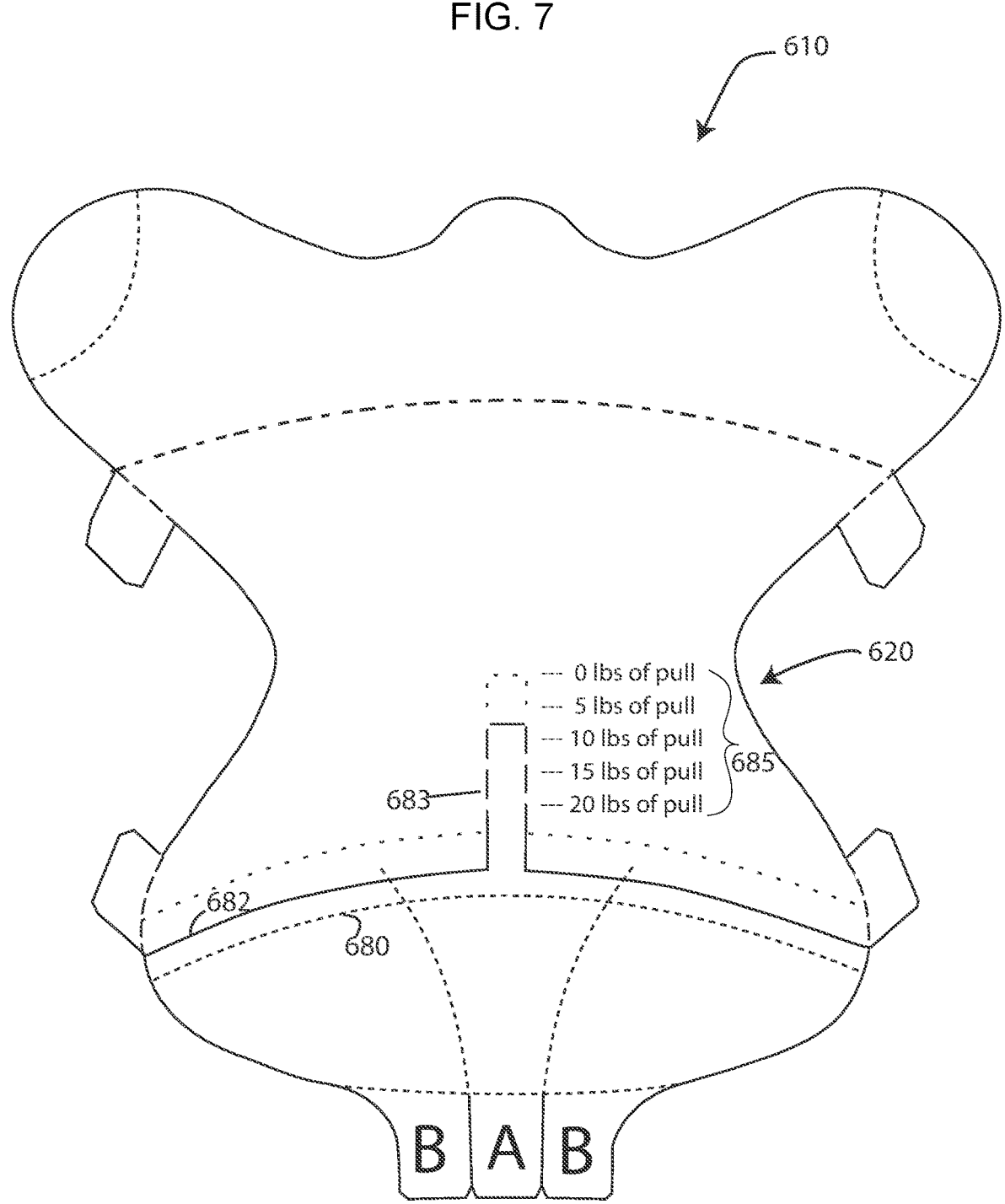
FIG. 7 shows an alternative retractor/wound exposure device which allows for stretching of the top layer of the device during application to the patient, with an original perforation line shown as a dashed ( - - - ) line and upon stretching as a dotted (•••) line, and wherein the device is provided with a tension gauge.
Figure 8:
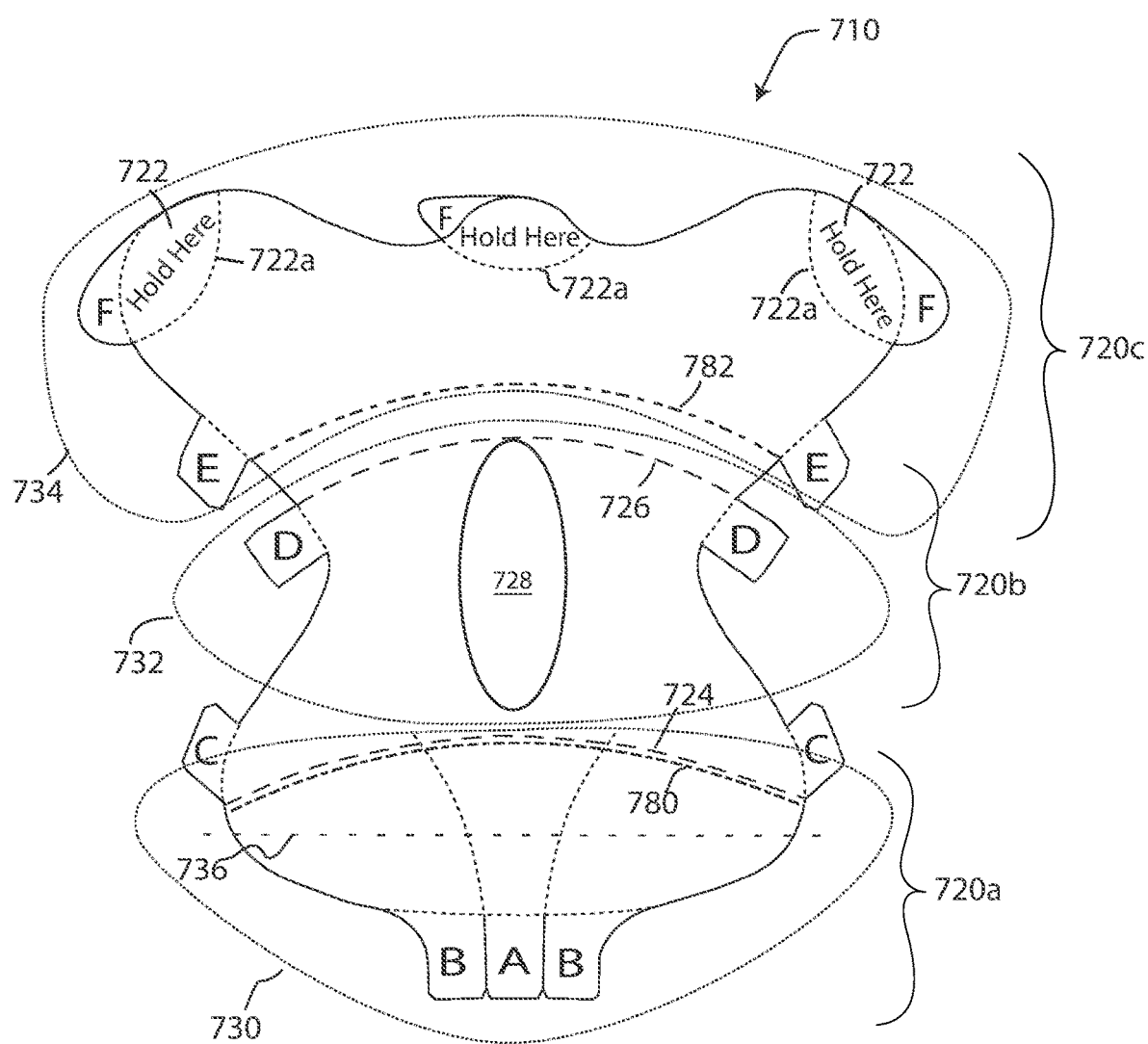
FIG. 8 is a plan view of a retractor/wound exposure device shaped similarly to the device of FIG. 7, but which is provided with the ability to remove a central transverse section of the top ply to allow for an enlarged stretch zone.

FIG. 8 shows a device 710 which a device is shaped similarly to the device 610 (FIG. 7). The device 710 includes two bottom ply cuts 780 and 782 which divide the backing, bottom ply of the device into three sections—a bottom section 720a, a middle section 720b and an upper section 720c. A- and B-tabs are provided along the bottom edge and are associated with the bottom ply (by top-middle cuts at the inner end of the tabs) such that the A- and B-tabs operate to remove the backing ply from the bottom section 720a in three pieces. C-tabs are provided along the sides of the middle section 720b and are associated with the bottom ply (by top-middle cuts at the inner end of the tabs) such that the C-tabs operate to remove the backing ply from the middle section. Finally E-tabs are provided along the sides of the upper section 720c and are associated with the bottom ply (by top-middle cuts at the inner end of the tabs) such that the E-tabs operate to remove the backing ply from the upper section 720c. The upper section is also provided with hand hold ("hold here") areas 722 which are defined by associated back cuts 722a. Thus the E-tabs remove the backing ply in the upper section except for in these hand hold areas, thereby providing a "protected" or adhesive free zone that can be grasped when the backing panel in the upper section has been removed. The hand hold areas 722 are provided with F-tabs to remove the backing layer in the hold here areas once the upper section 720c of the device has been adhered to the patient.

Additionally, the device 710 is provided with first and second top perforations 724 and 726, respectively. At least one D-tab is provided along a side of the middle section 720b and is associated with the top ply (by a bottom-middle cut at the inner end of the tab) such that the D-tabs operate to remove the top ply from the middle section in the area between the top perforations 724 and 726. In addition, a window 728 is formed between the perforated lines 724 and 726 by a through cut. The window (which is optional) can be provided to locally reduce the cross-sectional area to allow for stretch. This allows for adjusting the load lifting capability of the device.

In use, the bottom section 720a is initially applied to the patient. When applied, it bears a static load, and is not stretched. The static load area is defined by the lower area 730, defined by dashed lines. After the lower section 720a has been applied to the patient, the backing layer is removed from the middle section 720b by pulling on the C-tabs. With just the backing layer removed, the top ply will prevent the middle ply from stretching. However, if stretching is necessary during application of the device to a patient, the top ply strip between perforated lines 724 and 726 can be removed by pulling on the D-tab. This will expose a large strip or area of the middle ply, which can be stretched a desired amount. Once the middle section has been stretched and adhered to the patient, the backing layer can be removed from the top section 720c, and the top section can then be adhered to an anchor point on the patient.

As noted above, the bottom portion, identified by the dashed line 730 is subject to a static load. The central portion in which the top ply has been removed defines an area identified by the dashed line 732 which is subject to dynamic loads. The top section (which still has the top ply) defines an anchor attachment field load area, and is identified by the dashed line 734. When the device 710 is applied to the patient an imaginary theoretical load line 736 is effectively formed which extends through the bottom section and along which the forces are null. Below this null force line, linear forces are reduced, and above this null line, linear forces increase.

Figure 9:
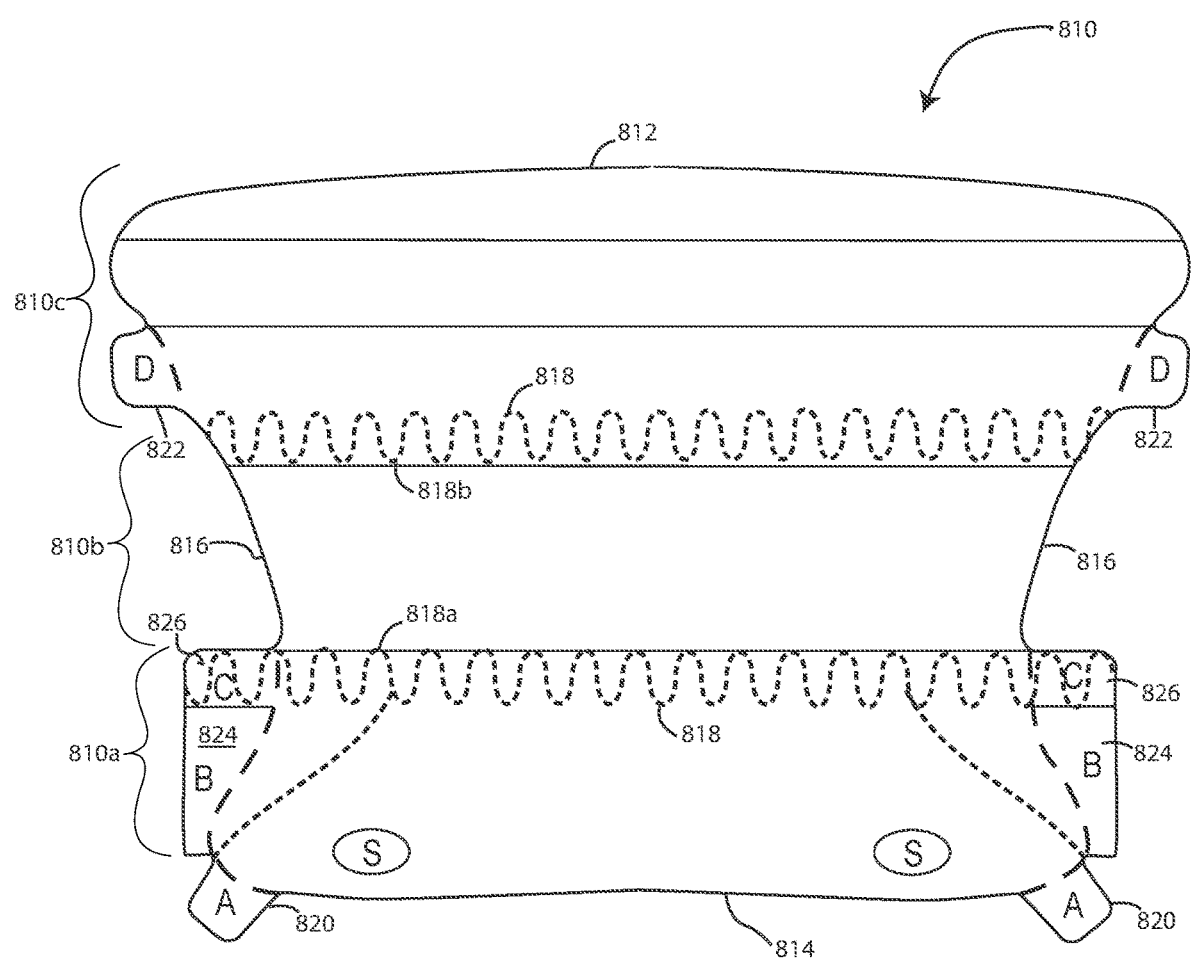
FIG. 9 is a plan view of a retractor/wound exposure device produced from three separate pieces of material.

FIG. 9 shows a multi-ply device 810 which is formed from three separate pieces of material which are joined together in a manufacturing or finishing process. The device has upper and lower edges 812 and 814, respectively and opposed side edges 816. The upper and lower edges are generally straight—although, as shown, the upper edge 812 has a slight convex curvature and the lower edge 814 has an even slighter concave curvature. The side edges 816 both define concavities. The device 810, as noted, is formed from three sections of material, and thus includes a bottom section 810a, a mid-section 810b, and an upper section 810c. The bottom and upper sections 810a,c are multi-ply sections, and can, for example, comprise three plies. The bottom and upper sections can, if desired, be formed from the same material. For example, the bottom and upper sections could be formed from a 3-ply material, such as, 3M tape 1583L. The mid-section 810b, on the other hand, is preferably made from a material that is different from the upper and bottom sections. The mid-section can, for example, be made from a single-ply non-adhesive material, such as 3M tape 9832F. In this manner, the upper and bottom sections can define anchor sections. The non-adhesive mid-section, which may not need adhesive for the device 810 to be used to maintain a patient's panniculus in a retracted position, may be more comfortable for the patient. The three sections can be joined together during a finishing process, as is known to those of skill in the art.

The device 810 is also shown to include a pair of spaced apart sinusoidal or wave shaped perforations 818. The wave or sinusoidal perforations 818 extend the width of the device. The upper wave perforation has trough bottoms 818b which are aligned with, or level with, the junction between mid-section 810b and the upper section 810c. The lower wave perforation has peaks 818a which are level or even with the junction between the mid-section 810b and the bottom section 810a. The wave perforations 818 are intended to reduce shear stresses on the patient's skin when the device is applied to the patient. The wave perforations 818 makes the shear line longer to reduce the concentrated adhesive area on the skin.

Additionally, the device 810 includes bottom ply A-tabs and D-tabs 822 which are formed and operable to remove the bottom ply (release liner) from the upper and bottom sections 810a,c. B-tabs 824 are formed and operable to remove the top ply from the device 810. Lastly, "press" down areas 826 (labeled "C") are provided adjacent the B tabs. As discussed above, these press down areas can be used (pressed against) when the B-tabs are pulled, to reduce the possibility of the middle ply from lifting off the patient when the top ply is removed from the device.

A further retractor/wound exposure device 910 is shown generally in FIG. 10A, which is designed to be worn post-operatively for extended periods of time to facilitate the healing of wounds that would otherwise be covered (over-lapped) by excess or redundant tissue (such as a panniculus). The retractor 910, as shown in FIG. 10B, comprises three plies—a bottom ply or release liner 912, a middle ply 914, and a top ply 916. The bottom ply 912 can, for example, be made from a low density polyethylene (LDPE) film. The middle ply is preferably stretchable and breathable (i.e., air permeable). It can be made from nylon, and can be woven or non-woven, or spun-laced. Further, it can include an elastic component, such as Spandex®, a polyester-polyure-thane copolymer. The middle ply is adhered to the bottom ply by a gel-type adhesive 913, such as a silicone gel adhesive. The top ply 916 is formed from a highly conformable film, such as an polyurethane, which is less stretchy than the middle ply. The top ply can, for example, be formed from a film available from 3M under the product code 9836. The top ply 916 is adhered to the middle ply by an adhesive acrylate 915.

As shown in FIG. 10B, and as will be discussed in more detail below, the device 910 includes top ply cuts TC which extend only through the top ply 916; bottom ply cuts BC which extend only through the bottom ply 912, top-middle ply cuts TMC which extend through the top and middle plies, but not through the bottom ply; bottom-middle ply cuts BMC which extend through the bottom and middle plies, but not through the top ply; and middle ply cuts MC which extend only though the middle ply. The addition of the middle ply cut MC is one of the features that distinguish the device 910 from the above-described devices.

To form the multi-ply device with the middle ply cuts MC, the middle ply material is first adhered to the bottom ply. This can be accomplished by applying the gel adhesive to the middle ply material, and then laminating the bottom ply material to the middle ply material; or by applying the gel adhesive to the bottom ply material and then laminating the middle ply material to the bottom ply material. If either the middle ply material or the bottom ply material is supplied with the gel adhesive, then the coating step can be avoided. With the middle and bottom plies joined, the middle ply cuts MC, the bottom ply cuts BC and bottom-middle cuts BMC are formed. The top ply material is then laminated to the bottom-middle ply assembly. This is accomplished by coating one of the top ply or middle ply with the acrylate adhesive, and then laminating the top ply material to the middle-bottom ply assembly. If either the top ply or middle ply is provided (as is) with the acrylate adhesive, then this coating step can be avoided. Once the top ply is adhered to the middle ply, the top ply cuts TC and top-middle cuts TMC can be formed. At the same time, the overall device 910 can be cut from the remainder of the material. As an alternative method, the middle ply and top ply can be adhered together first, and then the bottom ply can be laminated to the middle ply. The cuts are all preferably formed by die-cutting.

With reference to FIG. 10A, the device 910 has a top edge 922, a bottom edge 924, and generally concave side edges 926. The concavity of the side edges effectively forms a pair of upper lobes 928 and a pair of lower lobes 930. An A-tab 932 and two B-tabs 934 extend from the bottom of the bottom edge 924 of the device. The A-tab is shown to be generally centered, and the two B-tabs are adjacent opposite sides of the A-tab. Bottom ply cuts 936 extend from bottom edge 924 at the edges of the A-tab 932 (and from the inner edges of the B-tabs 934) to the side edges 926 of the device. As seen, the bottom cuts 936 are arced. A second bottom ply cut 938 extends between the opposed side edges 926 at approximately the narrowest width of the device. As seen, the bottom ply cut 938 has a slight upward concavity. An upper bottom cut 940 extends across the device above the bottom ply cut 938 and near the top of the device. As seen, the outer edges of the bottom ply cut 940 intersect the side edges of the device at the approximate bottom of the upper lobes 928, and arcs upwardly.

A pair of opposed C-tabs 942 extend from the side edges 926 between the bottom ply cuts 938 and 940. As shown, the bottom edges of the C-tabs are flush or even with the bottom ply cut 938. Additionally, a pair of D-tabs 944 extend from the upper lobes 928. As shown, the D-tabs extend downwardly and face the lower lobes 930. The A-, B-, C-, and D-tabs are all separated from the body of the device 910 by top-middle cuts 932a, 934a, 942a, and 944a, respectively. The bottom ply cuts 936 and 938 divide a bottom portion of the body bottom ply into a some-what T-shaped center portion 912a and two side lobes 912b, with the A-tab 932 being associated with the center portion 912a and the B-tabs 934 being associated with the two side lobes 912b. As can be appreciated from the discussion above, pulling of the A-tab 932 will remove the bottom ply portion 912a from the middle ply to expose the adhesive of the middle ply in this portion of the body; and pulling B-tabs will remove the bottom ply portions 912b from the middle ply to expose the adhesive of the middle ply in these sections.

The two bottom cuts 938 and 940 define a middle section 912c of the bottom ply with which the C-tabs 942 are associated. Pulling either C-tab will therefore remove the bottom ply portions 912c from the middle ply to expose the adhesive of the middle ply in this section.

Lastly, the portion 912d of the bottom ply between the bottom ply cut 940 and the top edge 922 of the device is associated with the D-tabs 944. Pulling the D-tabs removes the bottom ply portion 912d from the middle ply to expose the adhesive of the middle ply in this section.

A top ply cut 950 extends between the top edge 922 and bottom edge 924 of the device and effectively bi-sects that top ply of the device into two halves 916a and 916b. T1- and T2-tabs 952 and 954 extend from the top edge 922 of the device, and are separated from the body of the device by bottom-middle cuts 952a and 954a. The thus, the tabs 952 and 954 are co-extensive with, and are associated with, the top ply sections 916a and 916b, Hence, pulling the tabs 952 and 954 will pull the top ply sections 916a,b from the middle ply. Preferably, the adhesive will remain associated with the top ply, such that the exposed surface of the middle ply will be adhesive free, or at least non-tacky, when the top ply is removed. If desired, the top cut 950 could be omitted, and the top ply 916 could be removed from the middle ply as a single panel.

Lastly, the device 910 includes a middle cut 956 which extends between the side edges 926 of the device near the bottom edge 914. The middle cut 956 intersects the side edges generally at the top of the bottom lobes 930 and forms a generally downwardly curved arc.

The device 910 is preferably applied pre-operatively, in a bottom up fashion, much as described above in conjunction with the device 110. Initially, the A-tab is activated/pulled to remove the central portion 912a of the bottom ply from the device to expose the adhesive in this section. This central-lower section of the middle ply can then be applied to the patient by positioning the area on the panniculus (or other excess tissue) such that the bottom edge 924 of the device will be on the panniculus, and thus away from the intended incision site. This first section of the middle ply is then smoothed out over the patient's panniculus. The two side pieces 912b of the bottom ply are then removed by pulling the B-tabs. With the adhesive of the middle ply now exposed in the lower side portions, the side lower portions of the device can be smoothed over, and adhered to, the patient's panniculus.

After initial placement of the device in this manner, the device is folded over, and the C-tabs 942 are pulled to remove the middle panel 912c of the bottom ply from the middle ply, to expose the adhesive in this portion of the middle ply. This is accomplished with the middle portion of the device lifted or held away from the patient's skin. As can be appreciated, at this point in application of the device, the bottom ply portions 912d at the upper end of the device are still adhered to the middle ply, and thus, the top corners of the device, at this point, define grab or hand hold areas. This top portion of the device can then be used to pull the excess tissue (such as the panniculus) toward the anchor point. In a panniculus retraction, this would be in a cephalad direction relative to the patient. Because the top ply is relatively non-stretchy, the device will not stretch significantly, and the panniculus will be pulled away from the intended incision site to expose the intended incision site. When the panniculus has been pulled away from the incision site sufficiently, the middle portion of the middle ply can be applied to, and smoothed out over, the patient's skin. When the panniculus is released by the staff holding it in position, the device 910 will maintain the panniculus away from the incision site. At this point, the D-tabs can be pulled to remove the upper portion 912d of the bottom ply from the middle ply, and the top portion of the middle ply can be applied to the patient.

At this point, the bottom ply has been fully removed from the device, and the middle ply is adhered to the patient over the full extent of the middle ply, and the top ply remains on the middle ply. As noted above, the top ply is substantially non-stretchable, and hence, the top ply will prevent the panniculus from relaxing to a position in which the incision site is not accessible. Hence, the desired medical or surgical procedure can be carried out on the patient.

Once the procedure has been completed, it is desirable to maintain the panniculus away from the incision site to allow the incision to heal. As can be appreciated, if the panniculus was allowed to relax fully after the procedure, the incision site would be covered, air likely would not be able to flow to the incision site, and healing of the incision would be hampered. The device 910 can be worn long term (for several days or even weeks) to maintain the panniculus or other retracted excess tissue in a retracted position relative to the incision site.

The top ply is preferably air and water impermeable, but the middle ply is at least air permeable. The top ply is thus preferably removed from the middle ply after the procedure has been completed. The top ply is removed in two sections, 916a and 916b, using the T1- and T2-tabs 952 and 954. As noted above, there is a middle ply cut 956 at the bottom of the device. Thus, as the top ply is removed using the T1 and T2 tabs, the bottom portion 914a of the middle ply will be removed from the patient as well. The acrylic adhesive 915 is stronger than the gel adhesive 913 such that the bottom portion 914a of the middle ply will remain with the top ply as the top ply is removed. When the top ply is removed, all that will remain on the patient is the middle ply (less the bottom portion 914a of the middle ply). Removal of this bottom portion of the middle ply is intended to make the device more comfortable to wear for longer periods of time.

When the top ply is removed from the middle ply, the middle ply will be allowed to stretch according to its own stretch properties. However, the middle ply is not so stretchy that the patient's panniculus will fully relax. Even without the top ply, the middle ply will hold the panniculus away from the incision site to allow the incision to heal.

As noted above, the middle ply is adhered to the patient by a gel adhesive (preferably a silicone gel adhesive). Unlike a dry adhesive (such as the acrylate adhesive 915 which adheres the top ply to the middle ply), the gel adhesive protects the dermis from shear forces by accumulating the forces. Thus, forces that are transferred to the middle ply (which remains on the patient), for example, by the weight of the panniculus) are not transferred to the patient's dermis by the yielding properties of the gel adhesive. Dry adhesives, such as the acrylate adhesive 915 do not yield.

Figure 11:
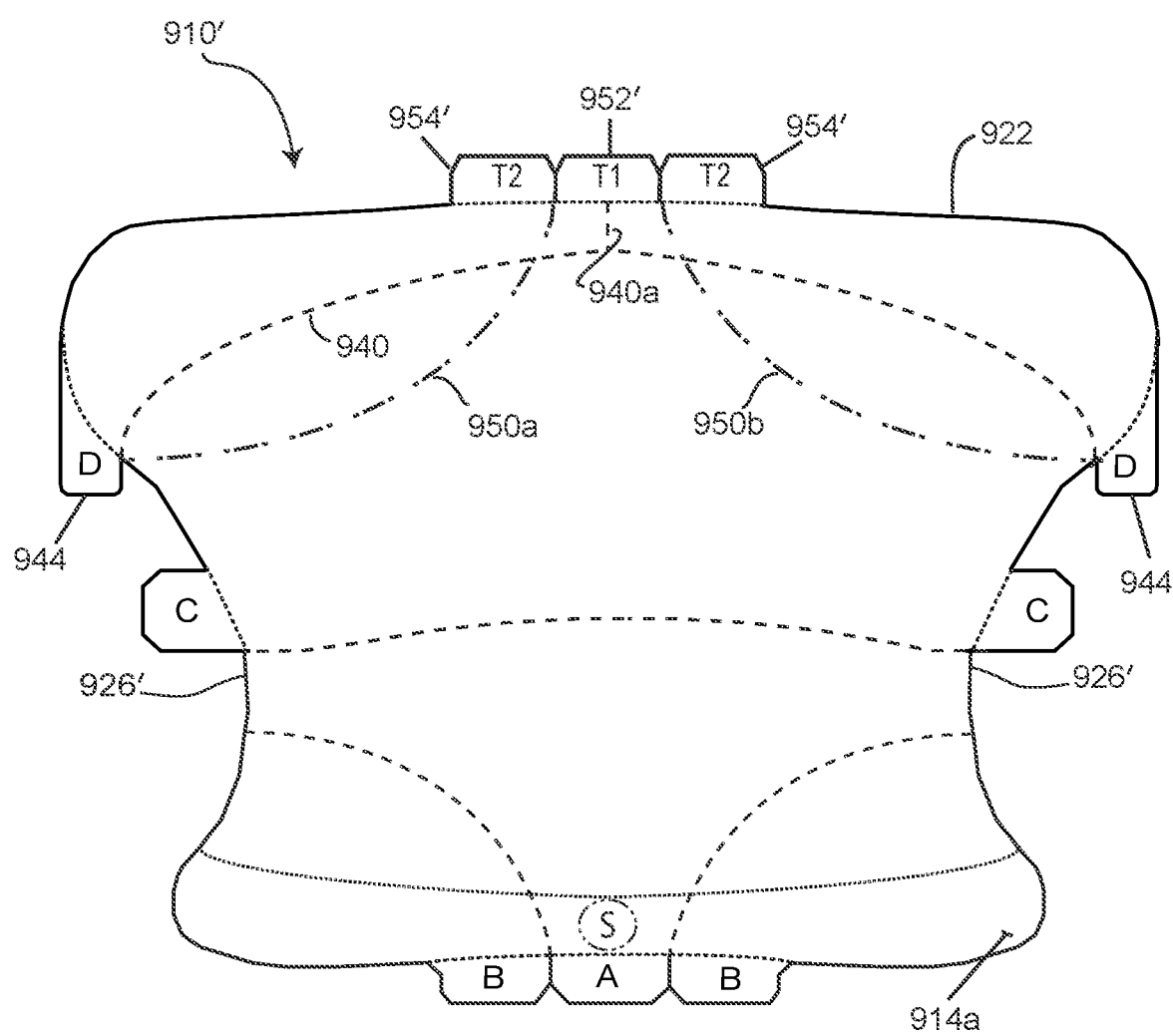
FIG. 11 is a variation of the device of FIG. 10.

A variation of the device 910 is shown in FIG. 11. The device 910' is substantially identical to the device 910. The only difference is in the top ply cuts. The device 910 has a single top ply cut 950 which extends top edge to the bottom edge and effectively bi-sects the top ply of the device 910. The device 910' omits the elongated top-to-bottom top cut, and replaces it with two arced top cuts 950a,b and includes a T1-tab 952' which is generally centered relative to the top edge 922' of the device 910', and two T2-tabs 954' positioned on either side of the T1-tab. The top cuts 950a,b extend from the top edge 922' of the device at the sides of the T1-tab to the side edge 926', and intersect the side edge 926' at approximately the same point where the bottom cut 940 intersects the side edge. The T1- and T2-tabs are separated from the body of the device by bottom-middle cuts, such that they will pull the top ply from the middle ply. The left side T2-tab will remove a left upper side portion of the top ply from the middle ply; the right side T2-tab will remove a right upper side portion of the top ply from the middle ply; and the T1-tab will remove the remainder of the top ply from the middle ply. With this variation, the entire bottom portion 914a of the middle ply will be removed with a single panel of the top ply (as compared to the device 910).

In addition, the device 910' includes a vertical bottom cut 940a which extends from the approximate middle of the bottom cut 940 to the top edge 922' of the device 910'. Thus, the two D-tabs will each remove one-half of the top portion of the bottom ply during application of the device to a patient.

Any of the above described devices can be provided with sensors or indicators to monitor and inform of, for example, changes in elongation and/or stretch of the device. Additionally, the device may include one or more sensor boards (including sensors) that monitors/collect and transmit data relative to ambient and physiological aspects of the patient's wound. For example, such sensors can monitor/detect the presence of biological (i.e., bacterial or viral) agents, physiological data (i.e., blood pressure, skin temperature at the incision site, heart rate), or concentrations of specific chemicals, vapors or gases (such as $H_2O$, $O_2$ or $CO_2$). Such sensors could also monitor the stretch/elongation of the retractor/stabilizer. Sensors and indicators which monitor elongation and/or stretch of the retractor/stabilizer can be placed anywhere on the device, and be used to monitor the stretch/elongation of the device in a direction of the tension of the device. This stretch direction could be, but is not necessarily, parallel to the machine direction of the device. Proposed locations for sensors/indicators are shown in FIGS. 1, 3, 9, 10, and 11 by an "S" on the devices. As seen, the sensors are shown to be near the bottom of the devices, to be located proximate the incision site. However, if desired, the sensor could be located elsewhere on the device.

An indicator/sensor which monitors or responds to elongation/stretch will provide an indication if the device exceeds more than a predetermined amount (percentage) of its maximum elongation/stretch. As can be appreciated, this can be beneficial during application of the device to the patient. Additionally, if the device is to be worn long term (i.e., for days, or even weeks), for example, after the top ply has been removed, an stretch/elongation indicator/sensor can determine if undue stresses are placed on the device which could affect the ability of the device to maintain the panniculus in a retracted position (and off a wound).

An indicator/sensor which monitors or measures ambient and physiological aspects of the patient's wound is preferably positioned on the device so as to be proximate the incision site. These indicators/sensors can be applied to the device after application of the device to the patient, or the device can be supplied with the sensor(s) already positioned on the device. Such an indicator/sensor would provide a notification if the monitored parameter exceeds or falls below a predetermined threshold. This can be relevant during a procedure. However, it can be more relevant if the device is worn long term. A rise in temperature or an increase in bacterial or viral activity can denote the infection has set in, or is setting in, at or around the incision site. A drop in $O_2$ levels or an increase in $H_2O$ levels could indicate that the incision site is not receiving enough air.

The stretch indicator can be mechanical, or as noted, incorporated in an electrical sensor. The sensor used in association with wound care is positioned to collect/monitor/assemble data relative to ambient conditions and physiological aspects of the patient and transmit the data to a receiver. The receiver can be a dedicated receiver or an application (app) on a personal device (tablet computer, mobile phone, etc.). Data collected is evaluated by the receiver to monitor ambient conditions at the incision site to determine the conditions at the incision site (wound).

If sensors are used, the device will be provided with a power source for the sensors. The sensors are wired or wireless and can be integrated into the device or placed in close proximity to the target site (either prior to or after the device has been applied the patient). The signal from the sensor will be received by a monitor/receiver which will interpret the signal. The monitor can, for example, be a personal device provided with an application (app) adapted to receive the signal from the sensor via, for example, blue tooth connectivity, or any other type of wireless connectivity. Alternatively, the monitor can be a dedicated monitor. The monitor can issue a visual, tactile (vibratory) or audible alert if the monitored parameter falls out of predetermined bounds. In addition to notifying the patient of an out of bounds parameter, the monitor can send a signal to a practitioner, so that the practitioner can receive warning of the out-of-bound condition. The practitioner can then take appropriate corrective actions as may be necessary.

In view of the above, it can be seen that we have provided a device which can initially be used as a retractor to retract and stabilize excess flesh (such as a panniculus) during a medical/surgical procedure. Upon completion of the procedure, the top ply of the device can be removed, leaving only the middle, breathable ply adhered to the patient. This middle ply can be worn for extended periods of time to maintain the excess flesh away from any incision site or puncture wound, to allow for proper healing. Additionally, the device is provided with tab configurations which allow for the bottom ply to be separated from the middle ply without the need for medical staff to contact adhesive of the middle ply. Further, the tab configuration allows for the top ply to be removed from the middle ply while the middle ply is adhered to the patient while minimizing the risk of removing the middle ply from the patient. Finally, variations are provided which enable the device to stretch during application to the patient, such that the middle ply can be relied upon to maintain a pull on the excess flesh to maintain the excess flesh in the retracted position.

As various changes could be made in the above constructions without departing from the scope of the invention, it is intended that all matter contained in the above description or shown in the accompanying drawings shall be interpreted as illustrative and not in a limiting sense. For example, although the device is shown with external tabs (which extend from the edges of the device), the device could be provided with internal tabs, wherein the outer edge of the tabs are flush with the edge of the device.

The invention claimed is:

1. A multi-ply adhesive device comprising:
a top layer, a backing layer and a middle layer between the top and backing layers; the middle layer being comprised of at least one middle ply and having a middle layer top surface and a middle layer bottom surface, said at least one middle ply being stretchable;
a middle-ply adhesive applied to substantially the entirety of the middle layer bottom surface to removably adhere the backing layer to the middle layer bottom surface;
at least one bottom ply tab integral with the device; the bottom ply tab comprising an inner edge defined by a cut extending through the top and middle layers such that when the at least one bottom ply tab is pulled away from the top and middle layers, at least a portion of the backing layer will be removed from the middle layer to expose the adhesive of the middle layer; and
at least one top ply tab integral with the device; the at least one top ply tab comprising an inner edge defined by a cut extending through the bottom and middle layers such that when the top ply tab is pulled away from the bottom and middle layers, at least a portion of the top layer will be removed from the middle layer.

2. The multi-ply adhesive device of claim 1 wherein said middle ply adhesive is a gel adhesive.

3. The multi-ply adhesive device of claim 2 wherein said gel adhesive is a silicone adhesive or a co-adhesive.

4. The multi-ply adhesive device of claim 1 wherein said top ply is adhered to said middle ply without adhesive.

5. The multi-ply adhesive device of claim 1 wherein said top ply is adhered to said middle ply with a top-ply adhesive which substantially covers a bottom surface of said top ply.

6. The multi-ply adhesive device of claim 5 wherein said top-ply adhesive is an acrylate adhesive or a co-adhesive.

7. The multi-ply adhesive device of claim 1 further including at least one "press" area at an edge of said device; said "press" area being defined by a top cut such that the top ply of said "press" area is not connected to the top ply of the remainder of the body; whereby, during use, said "press" area can be pressed against while the top ply tab is used to remove the top ply from the device to reduce the possibility of the middle ply from lifting off a patient during removal of the top ply.

8. The multi-ply adhesive device of claim 1 wherein the back ply is made from a material which is substantially non-stretchable.

9. The multi-ply adhesive device of claim 8 wherein the back ply is made from a paper or from an LDPE, PET or poly film.

10. The multi-ply adhesive device of claim 9 wherein the top and middle layers are polymers, and wherein the top layer is substantially not stretchable and the middle layer is stretchable, and preferably, highly stretchable.

11. The multi-ply adhesive device of claim 1 wherein the top layer is substantially fluid impermeable.

12. The multi-ply adhesive device of claim 1 wherein the middle layer is air permeable, such that said device is capable of being worn for extended periods of time.

13. The multi-ply adhesive device of claim 1 wherein said top ply tab at least partially overlaps said at least one bottom ply tab.

14. The multi-ply adhesive device of claim 1 wherein the device comprises a lower body portion and an upper anchor point portion.

15. The multi-ply adhesive device of claim 1 wherein said backing layer of said body portion has a plurality of back cuts, such that said backing layer defines a plurality of panels; said at least one bottom ply tab comprising a bottom ply tab for each of the backing layer panels.

16. The multi-ply adhesive device of claim 15 wherein at least two of said plurality of panels of said backing layer define a width which, at least in part is equal to the side-to-side width of said device.

17. The multi-ply adhesive device of claim 1 wherein said device is formed from a single piece of said material.

18. The multi-ply adhesive device of claim 1 wherein said device is formed from at least a first and a second piece of material.

19. The multi-ply device of claim 18 wherein said device is formed from a bottom section, a mid-section, and a top section which are joined together; at least said mid-section being formed from a material which is different than the material from which the top and bottom sections are formed.

20. The multi-ply device of claim 19 wherein said top and bottom sections are formed from the same material.

21. The multi-ply device of claim 19 wherein said mid-section is void of adhesive on a bottom surface of the mid-section.

22. The multi-ply device of claim 1 wherein said device includes at least one top cut which divides said top ply into at least two top ply panels; said device further including a top-ply tab associated with each top ply panel to remove said top-ply panels from said middle ply.

23. The multi-ply device of claim 1 including one middle ply cut; said middle ply cut extending only through said middle ply.

24. The multi-ply device of claim 23 wherein said middle ply cut extends across said device proximate the bottom edge of said device.

25. The multi-ply adhesive device of claim 1 further including an indicator/sensor adapted to monitor a parameter chosen from the group consisting of elongation and/or stretch of the retractor/stabilizer, and ambient and physiological aspects of the patient's wound; said indicator/sensor being adapted to indicate if said monitored parameter exceeds or falls below a predetermined threshold.

26. The retractor/stabilizer of claim 25 wherein said indicator/sensor monitors elongation/stretch of the retractor/stabilizer, said indicator/sensor being a mechanical indicator incorporated into the retractor/stabilizer.

27. The retractor/stabilizer of claim 25 wherein said indicator/sensor is an electrical sensor; said sensor transmitting to a receiver a signal indicative of the parameter being monitored.

28. A method of applying a multi-ply adhesive device of claim 1 to a pliable, flexible, retractable surface, the method comprising:
  removing the backing layer from the middle ply and adhering the device to the surface, such that the middle ply and top ply are applied to the surface to hold the surface in a desired retracted position;
  removing the top ply from the middle ply subsequent to application of the top and middle plies to the surface, whereby, after the top ply has been removed, the surface can return slightly from the retracted position.

29. The method of claim 28 wherein the pliable, flexible, retractable surface is excess or redundant tissue of a patient, and in particular, adipose tissue, breast tissue, or panniculus tissue.

30. The method of claim 29 wherein the middle ply is sufficiently strong to maintain the excess or redundant tissue in a retracted position relative to an incision site for an extended period of time.

31. The method of claim 30 wherein the middle ply can be worn for an extended period of time.

32. The method of claim 30 wherein the middle ply adhesive is a gel adhesive, whereby, forces generated by the weight of the excess or redundant tissue are transferred through the gel adhesive to the middle ply, such that the gel substantially protects the dermis of the patient from sheer forces generated by the weight of the excess or redundant tissue being evenly distributed to the dermis of the patient.

* * * * *